US 7,099,857 B2

(12) United States Patent
Lambert

(10) Patent No.: US 7,099,857 B2
(45) Date of Patent: *Aug. 29, 2006

(54) MULTI-ATTRIBUTE DRUG COMPARISON

(75) Inventor: Bruce L. Lambert, River Forest, IL (US)

(73) Assignee: BLL Consulting, Inc., River Forest, IL (US)

( * ) Notice: Subject to any disclaimer, the term of this patent is extended or adjusted under 35 U.S.C. 154(b) by 669 days.

This patent is subject to a terminal disclaimer.

(21) Appl. No.: 10/376,916

(22) Filed: Feb. 28, 2003

(65) Prior Publication Data

US 2003/0182101 A1 Sep. 25, 2003

Related U.S. Application Data

(63) Continuation-in-part of application No. 09/368,203, filed on Aug. 4, 1999, now Pat. No. 6,529,892.

(51) Int. Cl.
*G06F 17/00* (2006.01)
*G06F 15/18* (2006.01)
*G06F 7/00* (2006.01)

(52) U.S. Cl. .......................... 706/55; 706/48; 706/20; 707/5

(58) Field of Classification Search ................ 706/55; 704/1
See application file for complete search history.

(56) References Cited

U.S. PATENT DOCUMENTS

| 3,923,060 A | * | 12/1975 | Ellinwood, Jr. | .......... 604/891.1 |
|---|---|---|---|---|
| 4,382,277 A | | 5/1983 | Glaser et al. | |
| 4,384,325 A | | 5/1983 | Slechta, Jr. et al. | |
| 4,422,158 A | | 12/1983 | Galie | |

(Continued)

OTHER PUBLICATIONS

Lambert, B.: "Predicting look-alike and sound-alike medication errors", Am J. Health-Syst Pharm, vol. 54, May 15, 1997, pp. 1161-1171.

(Continued)

*Primary Examiner*—David Vincent
*Assistant Examiner*—Michael Caldwell
(74) *Attorney, Agent, or Firm*—Jagtiani + Guttag

(57) ABSTRACT

A computer-implemented apparatus or method, or a software product, for generating a composite quantitative comparison of drug products based on multiple attributes of them. A set of name-attribute similarity scores are generated based on similarities among the names of selected target and reference drugs. A set of product-attribute similarity scores are generated based on similarities among product attributes of the selected target and reference drugs. A target drug confusability score is generated based on the confusability of the target drug as compared to a population of other drugs. The composite quantitative comparison is generated based on a composite of the name-attribute and product-attribute similarity scores, and the target confusability score. A set of one or more severity of confusion scores may also be included in the composite quantitative comparison. These scores are based on one or more indicators of the severity of the consequences to a patient of confusing the target and reference drugs so that, for example, the wrong drug is administered to the patient, or the correct drug is incorrectly administered. The name-attribute similarity scores may be generated based on orthographic, phonetic, and/or phonological analysis. The product-attribute similarity scores may be generated based on the drugs' strengths, indications, dosages, administration routes, manufacturers, pharmacological categories, storage requirements, colors, shapes, legal standing, trademark description, and/or other attributes. The composite quantitative comparison may include severity-weighted similarity scores or both similarity scores and severity of confusion scores. The severity of confusion indicators may include a therapeutic index and/or a contraindication index.

47 Claims, 13 Drawing Sheets

U.S. PATENT DOCUMENTS

| | | | |
|---|---|---|---|
| 4,674,066 A | | 6/1987 | Kucera |
| 4,688,189 A | * | 8/1987 | Hirata .......................... 707/3 |
| 4,833,610 A | | 5/1989 | Zamora et al. |
| 5,297,039 A | | 3/1994 | Kanaegami et al. |
| 5,333,317 A | | 7/1994 | Dann |
| 5,365,455 A | * | 11/1994 | Tibbetts et al. ............... 702/20 |
| 5,416,696 A | | 5/1995 | Suzuoka |
| 5,701,466 A | | 12/1997 | Yong et al. |
| 5,802,508 A | | 9/1998 | Morgenstern |
| 5,845,255 A | * | 12/1998 | Mayaud ......................... 705/3 |
| 5,854,923 A | | 12/1998 | Dockter et al. |
| 5,898,586 A | | 4/1999 | Jeatran et al. |
| 5,937,400 A | | 8/1999 | Au |
| 6,009,397 A | | 12/1999 | Siegel |
| 6,243,501 B1 | | 6/2001 | Jamali |
| 6,529,892 B1 | * | 3/2003 | Lambert ...................... 706/55 |
| 2005/0027560 A1 | * | 2/2005 | Cook ........................... 705/2 |

OTHER PUBLICATIONS

U.S. Pharmacopeia, Appendix I: "Guiding Principles for Coining United States Adopted Names for Drugs", USP Dictionary of USAN and international drug names, 1998, pp. 867-875.

Lively, S., et al.: "Spoken Word Recognition Research and Theory", Handbook of Psycholinguistics, 1994, pp. 265-301.

Luce, P., et al.: "Similarity Neighborhoods of Spoken Words", Word Frequency Effects, 1990, pp. 122-147.

Booring, D., Rph., PhD, "The Development and Adoption of Nonproprietary, Established, and Proprietary Names for Pharmaceuticals", Drug Information Journal, vol. 31, 1997, pp. 621-635.

Hal, P.A.V.I et al.: "Approximate String Matching", ACM Computing Surveys, vol. 12, No. 4, Dec. 1980, pp. 111-132.

Stephen, G.: "String Distance and Common Sequences", String Searching Algorithms, Lecture Notes Series of Computing, vol. 3, pp. 39-87.

Cohen, M. "Drug product characteristics that foster drug-use-system errors", Am J. Health-Syst Pharm, vol. 52, Feb. 1995, pp. 395-399.

Lambert, L., et al.: "Predicting and Preventing Drug Name Confusion Errors: A Summary of Findings", Enhancing Patient Safety and Reducing Errors in Health Care, 1998, pp. 221-225, p. 215.

USP Quality Review—Use Caution—Avoid Confusion:, USP Practitioners' Reporting Network, May 1999, No. 6, pp. 1-4.

Luce, P. et al.: "Recognizing Spoken Words: The Neighborhood Activation Model", Ear and Hearing, vol. 19, No. 1, Feb. 1998, pp. 1-36.

Monsell, S.: "The Nature of Locus of Word Frequency Effects in Reading", Basic Processes in Reading, Visual Word Recognition, 1991, pp. 148-197.

Havens, L. et al.: "The Effect of Competition of Visual Duration Threshold and its Independence of Stimulus Frequency", Journal of Experimental Psychology, 1963, vol. 65, No. 1, pp. 6-11.

Grainger, J. Dijkstar, T.: "Visual Word Recognition: Models and Experiments", In: Dijkstra, T., de Smedt K, eds. Computational Psycholinguistics, 1996, pp. 139-165.

Grainger, J., Segui, J.: "Neighborhood frequency effects in visual word recognition: A comparison of lexical decision and masked identification latencies", Perception & Psychophysics, 1990, pp. 191-198.

Zobel, J., Dart P.: "Phonetic String Matching: Lessons from Information Retrieval", SIGIR96: Proceedings of the 19th Annual International ACM SIGIR Conference on Research and Development in Information Retrieval, Switzerland, Aug. 18-22, 1996, pp. 166-172.

Lambert, B., et al.: "Similarity as a Risk Factor in Drug Name Confusion Errors: The Look-Alike (Orthographic) and Sound-Alike (Phonetic) Model", Medical Care, in press, Mar. 1999, pp. 1-37.

Lambert, B., et al.: "Effects of Similarity of Pharmacists' Recall and Recognition of Drug Names", Pharm Sci 1998, 1:1333.

Grainger, J. et al.: "On the role of competing word units in visual word recognition: The neighborhood frequency effect", Perception & Psychophysics, 1989; 45:189-195.

Kohonen, T.: "Content-Addressable Memories", Second Edition New York: Springer-Verlag, 1987, pp. 19-27.

Kane, S.D.: "Trademark Law: A Practitioner's Guide" Practicing Law Institute, 1997, pp. 7/2-7/23.

Baddeley, A.D.: "The articulary loop", Working Memory, Oxford: Oxford University Press, 1986, pp. 75-107.

Lambert, Bruce L., "Automated Screening for Look-Alike and Sound-Aike Medication Errors," presentation Jan. 8, 1998 Food and Drug Administration conference: "Minimizing Medical Product Errors: A Systems Approach."

Executive Summary, "Minimizing Medical Product Errors: A Systems Approach," Jan. 8, 1998 Food and Drug Administration conference.

Winslett, Marianne, et al., "Formal Query Languages for Secure Rational Databases", ACM Transactions on Database Systems, vol. 19 No. 4, Dec. 1994, pp. 626-662.

* cited by examiner

| REC-ORD # | 214A DRUG IDENTIFIER | 214B NAME ATTRIBUTE | 214C COLOR ATTRIBUTE | 214D STRENGTH ATTRIBUTE | ---- | 214N TRADEMARK DESCRIPTION ATTRIBUTE |
|---|---|---|---|---|---|---|
| | | | DRUG ATRIBUTE DATABASE | | | |
| 1 | 214A-1 VALUE= "00001" | 214B-1 VALUE= "AMBIEN" | 214C-1 VALUE= "SALMON" | 214D-1 VALUE= "5 mg" | ---- | 214N-1 VALUE= "DRUG PRODUCT" |
| 2 | 214A-2 VALUE= "00002" | 214B-2 VALUE= "AMBIEN" | 214C-2 VALUE= "GRAY" | 214D-2 VALUE= "10 mg" | ---- | 214N-2 VALUE= "DRUG PRODUCT" |
| 3 | 214A-3 VALUE= "00003" | 214B-3 VALUE= "AMEN" | 214C-3 VALUE= "WHITE" | 214D-3 VALUE= "10 mg" | ---- | 214N-3 VALUE= "DRUG PRODUCT" |
| -- | ---- | ---- | ---- | ---- | ---- | ---- |
| M | 214A-M VALUE= "M" | 214B-M VALUE= "ZANTAC" | 214C-M VALUE= "YELLOW" | 214D-M VALUE= "300 mg" | ---- | 214N-M VALUE= "DRUG PRODUCT" |

| REC-ORD # | 222A DRUG IDENTIFIER | 222B NAME ATTRIBUTE | 222C COLOR ATTRIBUTE | 222D STRENGTH ATTRIBUTE | ---- | 222N TRADEMARK DESCRIPTION ATTRIBUTE |
|---|---|---|---|---|---|---|
| | | | TARGET-REFERENCE DATA | | | |
| 3 | 222A-3 VALUE= "00003" | 222B-3 VALUE= "AMEN" | 222C-3 VALUE= "WHITE" | 222D-3 VALUE= "10 mg" | ---- | 222N-3 VALUE= "DRUG PRODUCT" |
| M | 222A-M VALUE= "M" | 222B-M VALUE= "ZANTAC" | 222C-M VALUE= "YELLOW" | 222D-M VALUE= "300 mg" | ---- | 222N-M VALUE= "DRUG PRODUCT" |

MULTI-ATTRIBUTE DRUG COMPARISON

RELATED APPLICATIONS

The present invention claims priority to and is a Continuation-in-Part of U.S. patent application Ser. No.: 09/368,203, entitled "Apparatus, Method and Product for Multi-Attribute Drug Comparison," filed Aug. 4, 1999 now U.S. Pat. No. 6,529,892.

BACKGROUND OF THE INVENTION

1. Field of the Invention

The present invention relates generally to linguistic applications or attribute matching in information retrieval and data processing and, more particularly, to systems or methods for measuring similarities between words or between representations of multiple attributes of products or items, especially attributes related to pharmacological products or items.

2. Related Art

Errors in the administration of medications, such as occur when the wrong drug or the wrong dosage are provided to a patient, represent a serious problem that has been much discussed by health professionals, patient welfare groups, academics, insurers, and others. Various causes for these errors have been identified, including the misunderstanding of physicians' orders due to illegible handwriting, similarity between drug names, confusing pharmaceutical packaging, poor design of devices for administering drugs, and other factors. An overview of some systemic causes of medication errors is provided in M. R. Cohen, "Drug product characteristics that foster drug-use-system errors," 52 Am. J. Health-Syst Pharm (February 1995) pp. 395–399, hereafter referred to as "the Cohen article," which is hereby incorporated by reference in its entirety. Another overview of the subject is found in M. R. Cohen (ed.), *Medication errors*, American Pharmaceutical Association, Washington, D.C. (1999).

A variety of groups and government agencies have programs designed to identify the sources of medication errors and to reduce the likelihood of their occurrence. For example, the American Society of Hospital Pharmacists has issued "ASHP guidelines on preventing medication errors in hospitals," 50 Am. J. Hosp. Pharm. (1993) pp. 305–314; the U.S. Food and Drug Administration (FDA) has established a Subcommittee on Medication Errors; the National Coordinating Council for Medication Error Reporting and Prevention has information available on the Internet (www.usp.org/standard/9805/9805_08a.htm) and elsewhere; and a medication-error reporting network has been established by the nonprofit Institute for Safe Medication Practices and the Drug Product Problem Reporting Network of the U.S. Pharmacopeia, Inc. (USP).

One class of errors that has been identified and studied by these groups and agencies is related to the use of drug names that sound like, and/or look like, other drug names. Lists of these sound-alike or look-alike drugs have been published, as in N. M. Davis, et al., "Look-alike and sound-alike drug names: the problem and the solution," 27 Hosp. Pharm. (1992) pp. 95–98, 102–105, 108–110; and N. M. Davis, "Drug names that look and sound alike," in *Hospital Pharmacy*, vol. 32, pages 1558–70 (1997). Agencies such as the FDA, the United States Adopted Names Council (USAN), the International Nonproprietary Name (INN) Committee of the World Health Organization, the European Agency for the Evaluation of Medicinal Products (EMEA), and the U.S. Patent and Trademark Office (USPTO), have regulations and programs related to the possibility of confusion among drug names. Also, pharmaceutical companies typically expend significant effort in proposing and perfecting trademarks for new drugs.

Notwithstanding the activities of these, and other, organizations, new drugs continue to be given names that may be confused with those of existing drugs, not infrequently leading to serious or fatal consequences for patients. Confusion between Celebrex® and Celexa® is a recent example, as documented in *USP Quality Review*, May 1999, no. 66 (U.S. Pharmacopeia, Rockville, Md.). Also, existing look-alike or sound-alike drug names remain on the market. One reason for these continuing problems is the diverse, and sometimes conflicting, goals of the agencies and companies involved in the naming of drugs. For example, pharmaceutical companies seek trademarks based not just on the objective of distinguishing their drugs from the competition, but also on enhancing recognition and recall and creating brand loyalty. The USAN and the INN, although concerned with name confusion, are also interested in ensuring that drug names are useful to health care professionals, i.e., that drug names preferably convey some medical information rather than being merely arbitrary or fanciful. Similarly, the USP has an interest in encouraging the use of drug names that are consistent with the existing compendial nomenclature. In contrast, one element used by the courts and the USPTO to determine the likelihood of confusion between trademarks is the strength of a mark. A mark may be strong, and therefor entitled to broad protection, because it has a relatively remote relationship with the product, such as a mark that is arbitrary or fanciful.

Another reason for the continuing problem of drug name confusion is attributable simply to the large number of drugs available. For example, there are over 15,000 medications sold in the United States alone, and there are over 35,000 names in the U.S. Patent and Trademark Office's database of trademark registrations for pharmaceuticals. Approximately half a million pharmaceutical trademarks are registered in the major industrialized countries. Even agencies, such as the FDA, that are focused squarely on reducing medication errors due to name confusion are hard pressed to anticipate sources of name confusion due to the large number of pairs of proposed and existing names, proposed and proposed names, or existing and existing names.

Moreover, assessment of the likelihood of drug-name confusion often is limited by reliance on the subjective judgment of human experts. For example, the FDA employs panels of experts who are directed to make their evaluations based on guidelines that generally are open to subjective interpretation. The inevitable disagreements that arise result in what social scientists commonly refer to as "poor inter-rater reliability." Similarly, practitioners before the USPTO, and the examiners and other officials of that agency, must apply complex guidelines (statutory, regulatory, and judicial) that call ultimately for the application of subjective judgments.

Efforts have been made to systematize the analysis of drug names by human experts. For example, the Cohen article refers to a system used by the pharmaceutical industry "for assessing proposed trademarks for possible medication-error problems." 52 Am. J. Health-Syst Pharm (February 1995) p. 398. More generally, the same article refers to "a system for ranking pharmaceutical labeling and packaging for error potential." Id. at p. 399. Both systems appear to be based on the participation of experts who, in accordance with an evaluation protocol, apply conventional social-science rating techniques to some factors that are considered to be relevant to the potential for errors. For example, experts pronounce product names read from handwritten drug orders from physicians, and rank the potential for confusion on a scale of one to ten. Other experts assign point values to each factor. These scores for each factor may then be combined to provide an overall rating between one and ten that is intended to be indicative of the potential for confusion. Id. at p. 398. Although a quantitative rating is thus produced, this approach relies on the subjective judgment of experts. As is evident, the judgment of any person may vary on the same subject from one trial to another, and the judgments of two people may vary on the same subject. Thus, the approach is not deterministic in the sense that a particular input (a handwritten drug order, for example) may produce one output (the quantitative rating) for one trial and the same input may produce another output for another trial. Also, the approach is not "automatic" in the sense that determination of the quantitative rating requires human involvement.

Some computer-implemented techniques have been employed to provide a more objective, and automated, analysis of drug-name similarity. For example, pharmaceutical companies typically screen potential new drug names by computerized searching, apparently based on similarity of spelling and/or sound of the new drug names as compared with existing drug names. Typically, however, regulatory agencies do not require results of these searches to be submitted as part of the evaluation process. Trademark attorneys and commercial trademark-searching firms similarly use computer-based searching techniques, including Internet searching, to assess the likelihood that a registration for a proposed drug name will be granted by the USPTO. The utility to public agencies and the public of these search techniques is limited, however, by the fact that the precise methods by which the searches are conducted generally are not publicly disclosed. Consequently, due to this lack of transparency, and due to uncertainty as to whether the same or similar standards are applied to one or more searches by one or more firms, comparisons of the likelihood of confusion across a wide population of drugs is problematic or impracticable.

Moreover, these automated conventional techniques, have various characteristics that limit their efficacy in reducing confusion among drug names. For example, most of these techniques provide only an approximate relative measure. That is, the searching techniques may simply rank reference names in order of similarity to a target name. Thus, with respect to a target drug named "AAA," reference drug "AA" may be ranked first, reference drug "A" second, reference drug "AB" third, and so on. Moreover, if additional quantitative information is provided, it may be limited to a simple score that is not tied to a benchmark. That is, according to some conventional techniques, one pair of target and reference drugs may have a score of "1.2" and another pair a score of "0.7," but neither score provides any absolute measure of the likelihood of confusion. Rather, only a relative measure is provided by these techniques. That is, a score of 1.2 may indicate a higher likelihood of confusion, based on the names of the drugs, than a score of 0.7.

SUMMARY OF THE INVENTION

In one aspect of the invention, a drug comparator for assessing the confusability of one or more target drugs and one or more reference drugs based on one or more attributes of each target drug and each reference drug is disclosed. The drug comparator comprises a name attribute comparator that performs a composite quantitative comparison of a name attribute of the one or more target drugs and the one or more reference drugs and generates one or more name-attribute similarity scores based on said comparison. Each name-attribute similarity score represents a similarity of the compared name attributes, wherein the name attribute comparator comprises two or more analyzers selected from the group consisting of an orthographic analyzer that generates one or more name-attribute similarity scores based on one or more orthographic measures of the name attributes of the one or more target and reference drugs, a phonetic analyzer that generates one or more name-attribute similarity scores based on one or more phonetic measures of the name attributes of the one or more target and reference drugs, and a phonological analyzer that generates one or more name-attribute similarity scores based on one or more phonological measures of the name attributes of the one or more target and reference drugs.

In another aspect of the invention, a drug comparator for assessing the confusability of one or more target drugs and one or more reference drugs based on one or more attributes of each target drug and each reference drug is disclosed. The drug comparator comprises a product attribute comparator that performs a composite quantitative comparison of at least one product attribute of the one or more target drugs and the one or more reference drugs and generates one or more product-attribute similarity scores based on said comparison. Each product-attribute similarity score represents a similarity of the compared product attributes, wherein the product attribute comparator comprises any one or more comparators selected from the group consisting of a strength comparator that generates at least a first product-attribute similarity score based on one or more dosage strengths of the target and reference drugs, an indication comparator that generates at least a second product-attribute similarity score based on one or more indicated uses of the target and reference drugs, a dosage form comparator that generates at least a third product-attribute similarity score based on one or more dosage forms of the target and reference drugs, an administration route comparator that generates at least a fourth product-attribute similarity score based on one or more administration routes of the target and reference drugs, a manufacturer comparator that generates at least a fifth product-attribute similarity score based on one or more manufacturers of the target and reference drugs, a pharmacological category comparator that generates at least a sixth product-attribute similarity score based on one or more pharmacological categories of the target and reference drugs, a storage requirements comparator that generates at least a seventh product-attribute similarity score based on one or more storage requirements of the target and reference drugs, a color comparator that generates at least an eighth product-attribute similarity score based on one or more colors of the target and reference drugs, a shape comparator that generates at least a ninth product-attribute similarity score based on one or more shapes of the target and reference drugs, a legal standing comparator that generates at least a tenth product-attribute similarity score based on one or more legal standings of the target and reference drugs, a trademark description comparator that generates at least an eleventh product-attribute similarity score based on one or more goods and services trademark descriptions of the target and reference drugs, and a schedule comparator that generates at least a twelfth product-attribute similarity score based on one or more dosage intervals of the target and reference drugs.

In a further aspect of the invention, a drug comparator for assessing the confusability of one or more target drugs and one or more reference drugs based on one or more attributes of each target drug and each reference drug is disclosed. The drug comparator comprises a name attribute comparator that performs a composite quantitative comparison of a name attribute of the one or more target drugs and the one or more reference drugs and generates one or more name-attribute similarity scores based on said comparison. Each name-attribute similarity score represents a similarity of the compared name attributes. A product attribute comparator performs a composite quantitative comparison of at least one product attribute of the one or more target drugs and the one or more reference drugs and generates one or more product-attribute similarity scores based on said comparison, each product-attribute similarity score representing a similarity of the compared product attributes, wherein the drug comparator automatically generates the attribute similarity scores upon receipt of an indication of the one or more target drugs.

In yet another aspect of the invention, a drug comparator for assessing the confusability of one or more target drugs and one or more reference drugs based on one or more attributes of each target drug and each reference drug is disclosed. The drug comparator comprises a name attribute comparator that performs a composite quantitative comparison of a name attribute of the one or more target drugs and the one or more reference drugs and generates one or more name-attribute similarity scores based on said comparison. Each name-attribute similarity score represents a similarity of the compared name attributes, and a neighborhood density calculator calculates a neighborhood density score for at least a first target drug of the one or more target drugs based on a number of a first set of reference drugs, wherein each of the first set of reference drugs has a determined distance from the first target drug that is not greater than a threshold distance, wherein each determined distance is a function of the one or more attribute similarity scores.

In a further aspect of the invention, a drug comparator for assessing the confusability of one or more target drugs and one or more reference drugs based on one or more attributes of each target drug and each reference drug is disclosed. The drug comparator comprises a name attribute comparator that performs a composite quantitative comparison of a name attribute of the one or more target drugs and the one or more reference drugs, and generates one or more name-attribute similarity scores based on said comparison, each name-attribute similarity score representing a similarity of the compared name attributes, and a neighborhood familiarity calculator that calculates a neighborhood familiarity score for at least a first target drug of the one or more target drugs based on a familiarity of the first target drug and the familiarity of each of a first set of reference drugs, wherein each of the first set of reference drugs has a determined distance from the first target drug that is not greater than a threshold distance, wherein each determined distance is a function of the one or more attribute similarity scores.

It should be understood that a number of embodiments and implementations of the invention are possible, along with different aspects that may be included in each of the summarized embodiments. It should also be understood that the embodiments, implementations, and/or aspects are not necessarily inclusive or exclusive of each other and may be combined in any manner that is non-conflicting and otherwise possible. It should also be understood that these embodiments, implementations, and/or aspects of the invention are exemplary only and are considered to be non-limiting. Further, various embodiments, implementations, and/or aspects of the present invention provide certain advantages and overcome certain drawbacks of conventional techniques while other embodiments, implementations, and/or aspects provide the same or different advantages and overcome the same or other drawbacks in the same or different manner. Thus, not all embodiments, implementations, and/or aspects of the invention share the same advantages, and those that do may not share them under all circumstances.

BRIEF DESCRIPTION OF THE DRAWINGS

The above and further advantages of the invention will be more clearly appreciated from the following detailed description when taken in conjunction with the accompanying drawings, in which like reference numerals indicate like structures or method steps, in which the leftmost one or two digits of a reference numeral indicates the number of the figure in which the referenced element first appears (for example, the element 410 appears first in FIG. 4, the element 1020 first appears in FIG. 10), solid lines generally indicate control flow, dotted or dashed lines generally indicate data flow, rectangles generally indicate function elements or method steps, parallelograms generally indicate data objects, and wherein:

FIG. 2B is a simplified schematic representation of one embodiment of a drug attribute database generated, updated, and operated upon by the drug comparator of FIG. 2A;

FIG. 2C is a simplified schematic representation of one embodiment of an illustrative example of target-reference data generated by one embodiment of a target-reference data provider of the drug comparator of FIG. 2A;

DETAILED DESCRIPTION

Introduction

Figure 1:
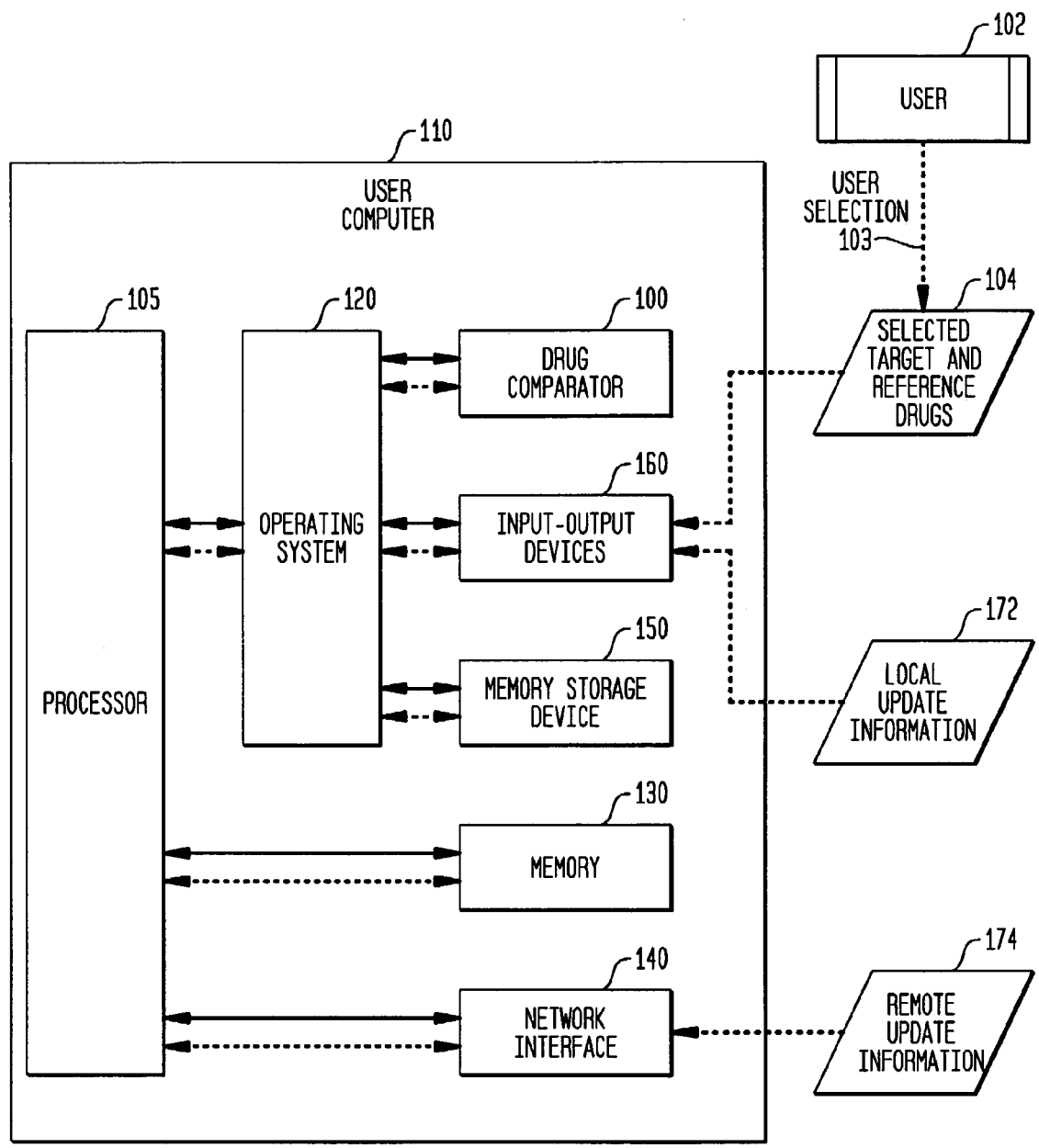
FIG. 1 is a functional block diagram of an illustrative user computer with which one embodiment of a drug comparator may be implemented.

The present invention is directed to comparing pharmaceutical drugs based on multiple attributes of the drugs. Comparisons between or among drugs may be based on the names of the drugs as well as a number of other attributes of the drug product. These other attributes are collectively referred to herein for convenience as "product attributes," as distinguished from a drug's "name attribute." For example, product attributes may include the dosage strengths of the drugs, their route of administration, or their color or shape. Additional specific examples are described below. A reason to include the product attributes of drugs in addition to their name attributes is that medication errors may arise not only because two drugs have similar names, but also because they physically resemble each other, are administered in a similar way, are made by the same company and thus have similar packaging or other similarities, and so on.

As used herein, the word "drug" will be understood to have a meaning that is possibly much broader than its ordinary dictionary meaning as applied to pharmaceutical drugs. In particular, "drug" will be understood to refer herein to any pharmaceutical drug, any biological preparation, and to any word or phrase (irrespective of the mode of communication), device, product, substance, method, procedure, or other item that may be the subject of medical communications, such as prescriptions. For example, a prescription may be written for a device, such as a hypodermic needle, or a product, such as a bandage. The confusion of one device for another device, or one product for another product, may have consequences that are as severe as the confusion of one pharmaceutical drug for another. Many of these devices, products, and so on, have both name and product attributes so that comparisons may be made for them, in accordance with the present invention, in essentially the same manner as comparisons may be made with respect to pharmaceutical drugs.

Moreover, the present invention may also be applied to deterministically provide quantitative comparisons between devices, products, substances, methods, procedures, and other items, that are not ordinarily the subject of medical communications. As one non-limiting example, the present invention may be used to quantify the likelihood of confusion between a product name related to a consumer Internet application with a product name related to a software application for use by developers of database software. The names of these illustrative products are not the only attributes that may be operated upon in accordance with the invention. Other "product" attributes may include, for example, the type of customer for whom the products are designed (i.e., consumers and software developers in this example), the type of market into which the products are sold (computer software in both cases), and so on.

The word "name" is used broadly herein. For example, a drug may have one or more generic names, chemical names, proprietary brand names, non-proprietary names, abbreviations, informal names, and so on. For background information in this regard, see D. Boring, "The development and adoption of nonproprietary, established, and proprietary names for pharmaceuticals," in *Drug Information Journal*, vol. 31, pages 621–634 (1997). Generally, the "name" of a drug, as used herein, may refer to any one or more words or symbols that are used to identify or describe a drug.

Comparisons generally are described herein as being made between one or more "target" drugs and one or more "reference" drugs. In one situation, a single target drug is compared to a single reference drug by analyzing their name and product attributes. The target drug may then similarly be compared to another reference drug, and so on through a list of reference drugs. These "one-to-one" comparisons may then be repeated for another target drug in relation to each of the reference drugs. In other situations, the attributes of a single target drug may be compared to composite attributes of two or more reference drugs; i.e., a "one-to-many" form of comparison. Similarly, the composite attributes of two or more target drugs may be compared to a single reference drug in a "many-to-one" form of comparison, or to the composite attributes of two or more reference drugs in a "many-to-many" form of comparison. For convenience, references typically are made herein simply to the one-to-one form of comparison, although it will be understood that these references generally could alternatively be stated in terms of any of the other forms. For example, the term "target-reference pair" may be used herein with reference to a one-to-one form of comparison of the attributes of an illustrative single target drug with an illustrative single reference drug. However, this term should be understood to also implicitly constitute an illustration of the other forms. For example, the term "target-reference pair" generally may also apply to the one-to-many form of comparison of the attributes of a single target drug with the composite attributes of two or more reference drugs. Similarly, for example, a description directed to a singular "reference drug" of the target-reference pair should be understood to include, in the illustrative alternative case of the one-to-many form, two or more reference drugs.

In some applications, such as when it is proposed to introduce a new drug to the market, the target drug may be the proposed new drug and the reference drug may be selected from a list of existing drugs. However, it need not be so; both drugs may be new drugs, both may be existing drugs, the target drug may be old and the reference drug new, or either may be categorized in a different way.

The word "comparison" and its grammatical variants, will be understood to have a broad meaning as used herein. Thus, a "comparison" may include processes such as statistical correlation; adaptive and other types of association; application of any mathematical or logical functions, including those derived analytically or those that may be learned from examples or by other adaptive methods (such as decision trees and any other learning method); or any other similar process or form of analysis that is now known or that may be developed in the future.

Moreover, a comparison of drugs need not be-limited to the purpose of assessing their similarity or, alternatively stated, the likelihood of confusion between them. For example, in some aspects of the invention, the target-reference pair may also be compared in order to determine a measure of the severity of confusion. For example, if the target-reference pair consists of information related to drugs A and B, and the erroneous substitution of drug B for drug A is likely to have fatal consequences, then there is a high measure of severity of confusion. In some implementations, the severity of confusion is combined with a measure of the similarity of the name and product attributes of the target-reference pair to provide a "severity-weighted similarity score." In other implementations, separate scores may be provided for the severity of confusion, and for the similarity, of each target-reference pair. In either case, the present invention has the additional advantage over conventional systems of providing a quantitative measure of the consequences of confusion. This measure may be integrated, or juxtaposed, with a quantitative measure of the likelihood of confusion.

Aspects of the invention also include a composite score generator that operates on the similarity scores, and optionally operates on the severity of confusion scores, to provide a composite quantitative comparison between the target and reference drugs. More specifically, the term "composite quantitative comparison" is used herein to refer to one or more quantitative measures of the similarity, and optionally of the severity of confusion, of a pair of target and reference drugs. This quantitative output of the invention is, at the least, a valuable adjunct to the exercise of human judgment. That is, even in those applications in which composite quantitative comparisons are provided to human experts for further processing or analysis, rather than relied upon directly, the decision-making process of the experts is greatly facilitated by the availability of objective information that has been generated deterministically and assembled based on a variety of relevant factors.

More specifically, some embodiments of the present invention (referred to hereafter as the "apparatus" embodiments), are directed to a drug comparator for comparing one or more target drugs with one or more reference drugs based on attribute data that describes a plurality of attributes of each target drug and each reference drug. The drug comparator includes a product attribute comparator that generates one or more product-attribute similarity scores representing a similarity of product attributes of a selected one or more target drugs and a selected one or more reference drugs. The drug comparator also includes a composite score generator that generates one or more composite quantitative comparisons based, at least in part, on one or more attribute similarity scores comprising the one or more product-attribute similarity scores.

The one or more composite quantitative comparisons are deterministic in typical implementations of these embodiments. The term "deterministic" is used in this context generally to mean that the outputs of the system or method of the present invention vary only if the inputs to the system vary. In more specific terms, an example may be assumed in which a user selects a particular drug A to be the target drug and drug B to be the reference drug. Because the system or method is deterministic, the one or more composite quantitative comparisons that are generated will be the same each time drugs A and B are selected, provided that there is no change in the input data regarding the attributes of the target and reference drugs (referred to herein as "target-reference data"). Thus, comparisons of the same drugs are replicable by different users and over periods of time. Similarly, a measure of the similarity, or of the severity of confusion, of a particular target-reference pair may be reliably compared to corresponding measures generated with respect to other target-reference pairs. That is, the results of these comparisons will not vary from one user to the next, or one trial to the next (if the target-reference data remain the same and the functions or steps of the system or method have not been changed). Another important benefit of this deterministic property is that regulators may make an objective assessment of the utility of the comparisons produced. If the comparisons are found to be helpful in identifying certain drugs subject to confusion (and optionally of having severe consequences of confusion), then the deterministic nature of the process used to generate these comparisons provides a degree of assurance that other confusing drugs will similarly be identified. This assurance generally is not present in non-deterministic systems in which human judgment, or other unpredictable factors, may influence the outcome.

A similar advantage of some embodiments of the present invention as compared to conventional systems and methods is that transparency and standardization are possible. Transparency in this context means that functions or steps in accordance with embodiments of the present invention generally may be precisely described and disclosed. Thus, users may form their own judgments as to how those functions or steps operate and whether they adequately take into account and/or process relevant information. Standardization means that, because of transparency, users may be confident that the same or equivalent functions or steps have been used to determine likelihood and/or severity of confusion from one target-reference pair to another, or between trials of the same target-reference pair.

After a user selects target and reference drugs, the one or more composite quantitative comparisons typically are automatically generated. That is, they may be generated in some implementations of the invention without any further involvement of the user. The present invention thus provides an advantage over conventional systems or methods that are not automated in this sense because the processing of the inputs to provide an output involves the use of humans to analyze facts and/or make decisions. Particularly when the human involvement is in the form of highly paid and busy experts, the savings in money and time due to automatic operation may be substantial. This advantage may be particularly important when a large number of target-reference pairs are involved. In particular, the system or method of the present invention generally provides a practical way for comprehensively comparing very large numbers of target and reference drugs. Similarly, comparisons of a particular target-reference pair with a large population of other target-reference pairs are possible due to automatic operation, typically carried out by a computer system. In contrast, a comprehensive comparison of large numbers of target and reference drugs may not be practicable using conventional systems or methods because of the time and/or expense involved.

In some further implementations, the invention includes a name attribute comparator that generates name-attribute similarity scores representing a similarity of name attributes of the selected target and reference drugs. The name-attribute similarity scores are a type of attribute similarity scores; that is, the attribute similarity scores may be made up partially, or entirely, of name-attribute similarity scores. In some aspects, the name attribute comparator includes an orthographic analyzer that generates a name-attribute similarity score based at least in part on one or more comparisons between orthographic representations of the names of the selected target and reference drugs. These comparisons may be based on N-gram measures and/or edit distance measures of orthographic similarity. In some aspects, the name attribute comparator may include a phonetic analyzer that generates a name-attribute similarity score based at least in part on phonetic measures of the names of the target and reference drugs. The term "phonetic measures" is used herein as a convenient way of indicating that phonetic transcription techniques are employed, and then a measure of orthographic similarity, such as N-gram measures or edit distance measures, are applied to the phonetically transformed representations. Also, in further aspects, the name attribute comparator includes a phonological analyzer that generates a name-attribute similarity score based at least in part on phonological measures of the names of the target and reference drugs. In some aspects, the name attribute comparator may have an orthographic analyzer, a phonetic analyzer, and a phonological analyzer.

In some implementations, the product attribute comparator of the drug comparator may include any combination of one or more of the following elements:
- a strength comparator that generates a product-attribute similarity score based at least in part on the dosage strengths of the target and reference drugs;
- an indication comparator that generates a product-attribute similarity score based at least in part on the indicated uses of the target and reference drugs;
- a dosage form comparator that generates a product-attribute similarity score based at least in part on the dosage forms of the target and reference drugs;
- an administration route comparator that generates a product-attribute similarity score based at least in part on the administration routes of the target and reference drugs;
- a manufacturer comparator that generates a product-attribute similarity score based at least in part on the manufacturers of the target and reference drugs;
- a pharmacological category comparator that generates a product-attribute similarity score based at least in part on the pharmacological categories of the target and reference drugs;
- a storage requirements comparator that generates a product-attribute similarity score based at least in part on the storage requirements of the target and reference drugs;
- a color comparator that generates an product-attribute similarity score based at least in part on the colors of the target and reference drugs;
- a shape comparator that generates a product-attribute similarity score based at least in part on the shapes of the target and reference drugs;
- a legal standing comparator that generates a product-attribute similarity score based at least in part on the legal standings of the target and reference drugs;
- a trademark description comparator that generates an product-attribute similarity score based at least in part on the goods and services trademark descriptions of the target and reference drugs; and
- a schedule comparator that generates at least a twelfth product-attribute similarity score based on one or more dosage intervals of the target and reference drugs.

In some embodiments, the drug comparator includes a neighborhood density calculator that calculates a neighborhood density score for at least a first target drug of the selected target drugs based on a number of a first set of reference drugs determined by their being a distance from the first target drug that is not greater than a threshold distance. These distances are determined by comparing one or more attributes of the corresponding reference drug with corresponding one or more attributes of the first target drug. These attributes could be any name attributes, any product attributes, and/or any combination thereof. In these embodiments, the composite score generator generates the one or more composite quantitative comparisons based, at least in part, on the neighborhood density score.

Also, the drug comparator may include a neighborhood familiarity calculator that calculates a neighborhood familiarity score for at least a first target drug of the selected target drugs based on a familiarity of each of a first set of reference drugs. The distance between each of the first set of reference drugs and the first target drug is not greater than a threshold distance. These distances are determined by comparing one or more attributes of the corresponding reference drug with corresponding one or more attributes of the first target drug. These attributes could be any name attributes, any product attributes, and/or any combination thereof In these embodiments, the composite score generator generates the one or more composite quantitative comparisons based, at least in part, on the neighborhood familiarity score. The confusability scores may be based at least in part on a first measure of familiarity that is based at least in part on the names of the first target drug and the names of the first set of reference drugs. Also, the first measure of familiarity may be determined by using frequency of prescription as a proxy for familiarity.

In yet further implementations, the drug comparator may include an attribute similarity scores processor that generates processed attribute similarity scores based at least in part on the attribute similarity scores. In these implementations, the composite score generator generates the composite quantitative comparisons based, at least in part, on the one or more attribute similarity scores by using the processed attribute similarity scores. In some aspects of these implementations, at least one attribute similarity score is associated with a weight, and the attribute similarity scores processor generates the processed attribute similarity scores at least in part by determining a weighted sum of one or more of the attribute similarity scores. The weight of the at least one attribute similarity score may be any of a variety of type of weights. For example, the weight may be a predetermined real number, a predetermined exponential of the corresponding attribute similarity score, a real number that is a function of one or more attribute similarity scores, an exponential of the corresponding attribute similarity score that is a function of one or more attribute similarity scores, and so on. More generally, the weight may be calculated, selected, designated, or otherwise determined based on any mathematical function, logical function, or hybrid mathematical/logical function, including those derived analytically and/or those that may be learned from examples or by other adaptive methods. For convenience of reference, the phrase "a type of weight determined by a mathematical/logical function" will be used herein to indicate any of these types of weights and/or combinations thereof.

The drug comparator may also include a severity of confusion scores generator that generates one or more severity of confusion scores representing a severity of confusion between the target and reference drugs. In these implementations, the composite score generator generates the composite quantitative comparisons based, at least in part, on the severity of confusion scores. In some aspects, a composite quantitative comparison may include severity-weighted similarity scores determined, at least in part, by weighting one or more of the processed attribute similarity scores by one or more of the severity of confusion scores. As used in this context, the term "weighting" includes modulating the processed attribute similarity scores by the severity of confusion scores in accordance with any known or later to be developed weighting technique including those that employ any mathematical and/or logical function. Also, the composite quantitative comparison may include a quantitative interpretation that compares a first set of one or more severity-weighted similarity scores corresponding to a first set of target and reference drugs to a second set of one or more severity-weighted similarity scores corresponding to a second set of target and reference drugs. The reference drugs of the first and second sets may be the same.

Furthermore, the composite quantitative comparison may include one or more processed attribute similarity scores and severity scores based on severity of confusion scores. In these implementations, the composite quantitative comparison may also include a quantitative interpretation that compares a first set of processed attribute similarity scores corresponding to a first set of target and reference drugs to a second set of processed attribute similarity scores corresponding to a second set of target and reference drugs. In some aspects, the composite quantitative comparison may have a quantitative interpretation that compares a first set of severity scores corresponding to a first set of target and reference drugs to a second set of severity scores corresponding to a second set of target and reference drugs.

In some implementations, the severity of confusion scores generator includes a therapeutic index comparator that generates a severity of confusion score based, at least in part, on a therapeutic index of one or more of the target and reference drugs. Also, the therapeutic index comparator may generate a severity of confusion scores based, at least in part, on a contraindication index of one or more of the target and reference drugs.

Typically, the composite quantitative comparisons include a measure of the absolute (as opposed to a solely relative) likelihood of confusing the selected target drugs with the selected reference drugs. That is, the composite quantitative comparisons provide a measure against one or more benchmark values of confusion. For example, a processed attribute similarity score (or, as explained below, a severity-weighted similarity score or un-processed attribute similarity score) of 0.5 may be provided for a target-reference pair of drugs A and B, and a similar type of score of 6.2 for the drugs A and C. These values may be compared to similar types of scores for large numbers of other target-reference pairs. Any of a variety of known statistical techniques may be applied to compare these two drug pairs to the larger population of drug pairs in terms of their respective scores. Thus, it may be determined, in accordance with these implementations, that drugs A and C not only are more likely to be confused than drugs A and B (a solely relative measure), but also that the score of 6.2 for drugs A and C represents a very high likelihood of confusion (what is referred to herein as an "absolute" measure). This feature allows for more meaningful interpretation of comparison data than generally is the case with respect to conventional systems or methods.

In this example, the absolute measure may be determined based on a comparison of the drug pair consisting of drugs A and C with many, or even all, of the drug pairs that may be constructed from the target-reference data. Thus, it may be determined that the similarity, or likelihood of confusion, of drugs A and C is in the 99th percentile with respect to the likelihood of confusion as measured across a large population of target-reference pairs. As noted, this type of comprehensive comparison typically is not done in conventional systems because, among other reasons, the large number of comparisons makes the task impracticable in view of the time, and possibly expense, involved. Also, the measure of the likelihood of confusion determined in accordance with some embodiments may be based on one or more experimentally determined benchmarks. For example, experiments may have been conducted under controlled circumstances that indicate that the actual likelihood of confusing drugs A and C is very high as compared with the likelihood of confusing a number of other drug pairs. Thus, the similarity score of 6.2 for drugs A and C obtained in accordance with the preceding example may be identified as representing a value in the high range of confusability. Thus, even if no experimental data is available with respect to the likelihood of confusion of another target-reference pair of drugs A and E, they may be viewed as having a very high likelihood of confusion if they have a similarity score of 6.3. The similarity scores of drug pairs may also be scaled in accordance with one or more benchmarks of this type.

In other embodiments of the invention (referred to hereafter as "method" embodiments), a method, is described for comparing one or more target drugs with one or more reference drugs based on attribute data that describes a plurality of attributes of each target drug and each reference drug. The method includes the steps of: (1) generating product-attribute similarity scores representing a similarity of product attributes of selected target and reference drugs; and (2) generating composite quantitative comparisons based, at least in part, on attribute similarity scores including the product-attribute similarity scores. In some implementations of this method, the composite quantitative comparisons are deterministic. In some aspects, this method may also include the step of (3) generating name-attribute similarity scores representing a similarity of name attributes of the selected target and reference drugs. In these aspects, the attribute similarity scores also include the name-attribute similarity scores. Other implementations and aspects of these methods generally parallel the implementations and aspects of the apparatus embodiments of the present invention, summarized above.

Yet other embodiments of the present invention are directed to a storage medium that contains software that, when executed on a computing system, performs a method for comparing one or more target drugs with one or more reference drugs based on attribute data that describes a plurality of attributes of each target drug and each reference drug. The methods practiced in accordance with various implementations of these embodiments may correspond to all or some of the methods of the methods embodiments, summarized above.

Further embodiments of the present invention are directed to a product that includes a composite quantitative comparison of one or more target drugs with one or more reference drugs based on attribute data that describes a plurality of attributes of each target drug and each reference drug. The composite quantitative comparison is generated by various methods that may correspond to all or some of the methods of the methods embodiments, summarized above.

Yet other embodiments of the present invention are directed to a computer-implemented system for comparing one or more target drugs with one or more reference drugs. The system includes (1) a target-reference data provider that provides target-reference data describing a plurality of attributes of each target drug and each reference drug; and (2) a composite analyzer that generates one or more composite quantitative comparisons of a selected one or more target drugs and a selected one or more reference drugs. The composite quantitative comparisons may be deterministic. The composite analyzer includes (a) an attribute similarity scores generator that generates one or more attribute similarity scores representing a similarity of attributes of the selected target and reference drugs. The attribute similarity scores generator includes any one or more attribute comparators selected from the group consisting of:

a strength comparator that generates an attribute similarity score based at least in part on the dosage strengths of the target and reference drugs;

an indication comparator that generates an attribute similarity score based at least in part on the indicated uses of the target and reference drugs;

a dosage form comparator that generates an attribute similarity score based at least in part on the dosage forms of the target and reference drugs;

an administration route comparator that generates an attribute similarity score based at least in part on the administration routes of the target and reference drugs;

a manufacturer comparator that generates an attribute similarity score based at least in part on the manufacturers of the target and reference drugs;

a pharmacological category comparator that generates an attribute similarity score based at least in part on the pharmacological categories of the target and reference drugs;

a storage requirements comparator that generates an attribute similarity score based at least in part on the storage requirements of the target and reference drugs;

a color comparator that generates an product-attribute similarity score based at least in part on the colors of the target and reference drugs;

a shape comparator that generates an attribute similarity score based at least in part on the shapes of the target and reference drugs;

a legal standing comparator that generates an attribute similarity score based at least in part on the legal standings of the target and reference drugs;

a trademark description comparator that generates an attribute similarity score based at least in part on the goods and services trademark descriptions of the target and reference drugs;

a name attribute comparator that generates an attribute similarity score based at least in part on one or more names of the target and reference drugs; or a schedule comparator that generates at least a twelfth product-attribute similarity score based on one or more dosage intervals of the target and reference drugs.

In some implementations, the name attribute comparator includes any one or more name attribute analyzers selected from the group consisting of:

an orthographic analyzer that generates an attribute similarity score based at least in part on orthographic measures of the names of the selected target and reference drugs;

a phonetic analyzer that generates an attribute similarity score based at least in part on phonetic measures of the names of the target and reference drugs; or a phonological analyzer that generates an attribute similarity score based at least in part on phonological measures of the names of the target and reference drugs.

The composite analyzer may also include a composite score generator that generates the composite quantitative comparisons based, at least in part, on the attribute similarity scores. In further implementations, the composite analyzer may also include a severity of confusion scores generator that generates severity of confusion scores representing a severity of confusion between the target and reference drugs. In these implementations, the composite score generator generates the composite quantitative comparisons based, at least in part, on the severity of confusion scores.

In yet further embodiments, the composite analyzer may also have a neighborhood density calculator that calculates a neighborhood density score for at least a first target drug of the selected target drugs based on a number of a first set of reference drugs determined by their being a distance from the first target drug that is not greater than a threshold distance. These distances are determined by comparing one or more attributes of the corresponding reference drug with corresponding one or more attributes of the first target drug. These attributes could be any name attributes, any product attributes, and/or any combination thereof. In these embodiments, the composite score generator generates the one or more composite quantitative comparisons based, at least in part, on the neighborhood density score.

Also, the composite analyzer may include a neighborhood familiarity calculator that calculates a neighborhood familiarity score for at least a first target drug of the selected target drugs based on a familiarity of each of a first set of reference drugs. The distance between each of the first set of reference drugs and the first target drug is not greater than a threshold distance. These distances are determined by comparing one or more attributes of the corresponding reference drug with corresponding one or more attributes of the first target drug. These attributes could be any name attributes, any product attributes, and/or any combination thereof. In these embodiments, the composite score generator generates the one or more composite quantitative comparisons based, at least in part, on the neighborhood familiarity score. The confusability scores may be based at least in part on a first measure of familiarity that is based at least in part on the names of the first target drug and the names of the first set of reference drugs. Also, the first measure of familiarity may be determined by using frequency of prescription as a proxy for familiarity.

In some embodiments, the computer system includes an attribute database updater that updates a target and reference drugs attribute database. This database includes data regarding attributes of the target and reference drugs. In these embodiments, the target-reference data provider provides the target-reference data based on the updated target and reference drugs attribute database.

In yet other embodiments, the invention is directed to a multi-attribute comparator for comparing one or more target items with one or more reference items based on attribute data that describes a plurality of attributes of each target item and each reference item. These target and reference items need not ordinarily pertain to pharmaceutical drugs or medically related communications. The multi-attribute comparator includes a product attribute comparator that generates one or more product-attribute similarity scores representing a similarity of product attributes of a selected one or more target items and a selected one or more reference items. The multi-attribute comparator also has a composite score generator that generates one or more composite quantitative comparisons based, at least in part, on one or more attribute similarity scores comprising the one or more product-attribute similarity scores. The one or more composite quantitative comparisons are deterministic.

The attributes of the present invention and its underlying method and architecture will now be described in greater detail with reference to an illustrative embodiment of the invention, referred to as a drug comparator 100. Aspects of comparator 100 are shown in FIG. 2A through FIG. 9, and corresponding method steps are shown in FIG. 10. Comparator 100, in the illustrated embodiment, operates as an element of a user computer 110, shown in FIG. 1.

Various functional elements of the present invention are described with respect to the illustrated embodiment that may be implemented either in software, hardware, firmware, or any combination thereof. For convenience of illustration, descriptions generally are made with respect to implementations in software. Such descriptions therefore typically refer to software-implemented functional elements that will be understood to comprise sets of software instructions that cause the described functions to be performed. For example, in a software implementation, comparator 100 may be considered to be a set of drug-comparator instructions. Similarly, a functional element of comparator 100, such as attribute similarity scores generator 310, may be considered to be a set of attribute-similarity-scores-generator instructions.

It will be understood by those skilled in the relevant art that the functions ascribed to comparator 100 of the illustrated embodiment, or any of its functional modules, typically are performed by a central processing unit (CPU) of a computer, such as processor 105 of user computer 110 of FIG. 1, executing portions of the set of drug-comparator instructions, typically in cooperation with the operating system of the computer. More generally, it will be understood that functions performed by the invention, whether implemented in software, hardware, firmware, or any combination thereof, typically are performed by the CPU in cooperation with the operating system, or by a special purpose processor. Henceforth, the fact of such cooperation among the CPU (or a special purpose processor) and the operating system, and the elements of the invention, whether implemented in software, hardware, firmware, or any combination thereof, may therefore not be repeated or further described, but will be understood to be implied.

USER COMPUTER 110

FIG. 1 is a simplified functional block diagram of one embodiment of a user computer 110, upon which drug comparator 100 of the illustrated embodiment may be implemented. User computer 110 may be any type of computer system, such as a personal computer, workstation, network server, or other computer platform now or later developed. Alternatively, user computer 110 may be a device specially designed and configured to support and execute the functions of comparator 100.

As shown in FIG. 1, user computer 110 includes known components such as a processor 105, operating system 120, memory 130, network interface 140, memory storage device 150, and input-output device 160. It will be understood by those skilled in the relevant art that there are many possible configurations of these components and that some components that may typically be included in user computer 110 are not shown, such as a video card, data backup unit, and many other devices.

Processor 105 may be a commercially available processor such as a Pentium or Celeron microprocessor from Intel Corporation, a PA-RISC processor made by Hewlett-Packard Company, a SPARC® processor made by Sun Microsystems, a 68000 series microprocessor made by Motorola, an Alpha processor made by Digital Equipment Corporation, or it may be one of other processors that are or will become available. Processor 105 executes operating system 120, which may be, for example, one of the MS-DOS, Windows 3.1, Windows for Work Groups, Windows 95 or 98, or Windows NT operating systems from the Microsoft Corporation; the System 7 or System 8 operating system from Apple Computer; the Solaris operating system from Sun Microsystems; a Unixg®-type operating system available from many vendors such as Sun Microsystems, Inc., Hewlett-Packard, or AT&T; the freeware version of Unix® known as Linux; another or a future operating system; or some combination thereof. Operating system 120 interfaces with firmware and hardware in a well-known manner, and facilitates processors 105 in coordinating and executing the functions of the other components of user computer 110. In other implementations, a computer system need not have a CPU and/or an operating system.

Memory 130 may be any of a variety of known or future memory devices, including, for example, any commonly available random access memory (RAM). Memory storage device 150 may be any of a variety of known or future devices, including a compact disk drive, a tape drive, a hard disk drive, a removable hard disk drive, or a diskette drive. Such types of memory storage device 150 typically read from, and/or write to, a program storage medium (not shown) such as, respectively, a compact disk, magnetic tape, hard disk, removable hard disk, floppy diskette, or other storage medium. Any such program storage medium may be a computer program product. As will be appreciated, such program storage media typically have stored therein a computer software program and/or data.

Computer software programs, also called computer control logic, typically are stored in memory 130 and/or the program storage device used in conjunction with memory storage device 150. Such computer software programs, when executed by processor 105, enables user computer 110 to perform the functions of the present invention as described herein. Accordingly, such computer software programs may be referred to as controllers of user computer 110.

In one embodiment, the present invention is directed to a computer program product comprising a computer usable storage medium having control logic (computer software program, including program code) stored therein. The control logic, when executed by processor 105, causes user computer 110 to perform the functions of the invention as described herein. Alternatively, in accordance with another embodiment of the present invention, the control logic causes computer 110 to perform a method for comparing target and reference drugs. In another embodiment, the present invention is implemented primarily in hardware using, for example, a hardware state machine. Implementation of the hardware state machine so as to perform the functions described herein will be apparent to those skilled in the relevant arts.

Input devices of input-output devices 160 could include any of a variety of known devices for accepting information from a user, whether a human or a machine, whether local or remote. Such devices include, for example a keyboard, mouse, touch-screen display, touch pad, microphone with a voice recognition device, or modem. Output devices of input-output devices 160 could include any of a variety of known devices for presenting information to a user, whether a human or a machine, whether local or remote. Such devices include, for example, a video monitor, printer, audio speaker with a voice synthesis device, or modem. Input-output devices 160 could also include any of a variety of known removable storage devices, including a compact disk drive, a tape drive, a removable hard disk drive, or a diskette drive.

Various operations of comparator 100, in one embodiment, may be implemented in the LISP, C, and/or C++ programming languages. It will be understood by those skilled in the relevant art, however, that many other programming languages could also be used. Also, as noted, comparator 100 of the illustrated embodiment is executed on user computer 110 and may be implemented in any combination of software, hardware, or firmware. If implemented in software, comparator 100 may be loaded into memory 130 and/or memory storage device 150 through one of input-output devices 160. All or portions of comparator 100 may also reside in a read-only memory or similar device of memory 130 and/or memory storage device 150, such devices not requiring that comparator 100 first be loaded through input-output devices 160. It will be understood by those skilled in the relevant art that comparator 100, or portions of it, typically are loaded by processor 105 in a known manner into memory 130, and/or a cache memory (not shown), as advantageous for execution. Also, it will be understood that all or portions of comparator 100 may, in alternative embodiments, be located on, or distributed across, computer systems other than or in addition to user computer 110. All or portions of comparator 100 may also be executed in multiple instances of its constituent tasks on parallel or distributed processors (not shown).

DRUG COMPARATOR 100

Figure 2A:
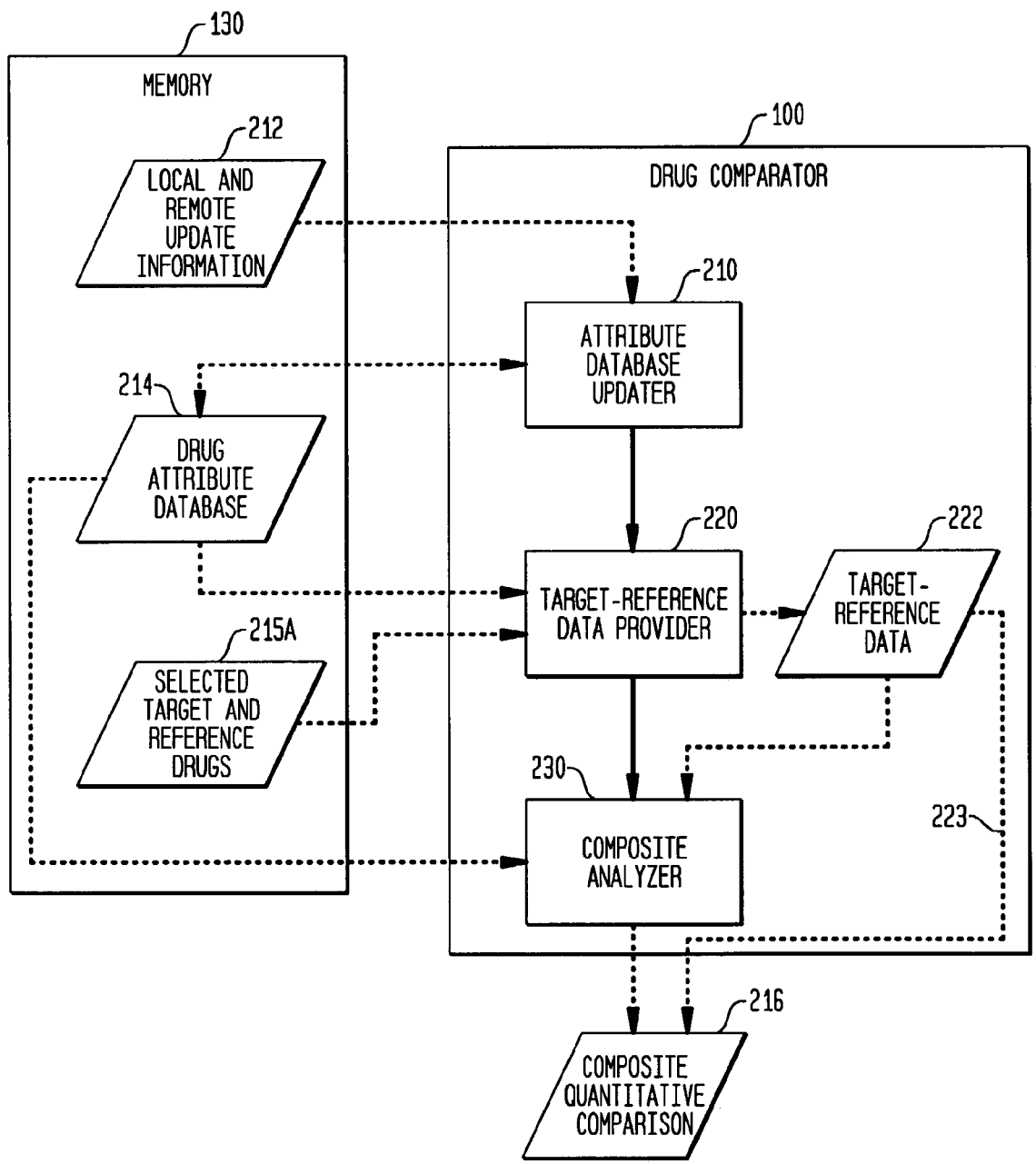
FIG. 2A is a functional block diagram of the drug comparator of FIG. 1, including its connections to one embodiment of a memory of the user computer of FIG. 1.

FIG. 2A is a functional block diagram of drug comparator 100. Comparator 100 compares one or more selected target drugs with one or more selected reference drugs. This comparison is based on data that describes the attributes of the target and reference drugs. In the illustrated embodiment, comparator 100 includes an attribute database updater 210 that updates a drug attribute database 214 that includes data describing the attributes of drugs. Comparator 100 also has a target-reference data provider 220 that provides target-reference data 222 for selected target and reference drugs based on updated database 214. Data 222 describes the attributes of each of the selected target and reference drugs. Also included in comparator 100 is composite analyzer 230 that, based on data 222, generates a composite quantitative comparison 216 of the selected target and reference drugs. Each of these elements of comparator 100 is now described in greater detail.

ATTRIBUTE DATABASE UPDATER 210

As noted, attribute database updater 210 updates drug attribute database 214, which may be any kind of database, including a relational database, object-oriented database, unstructured database or other database; a data file or group of data files; a data stream; and/or any other known or yet-to-be developed structure or technique, whether local or remote, distributed or non-distributed, for providing access to data for use in a computing system. It will also be understood that the information stored in database 214 may, in alternative embodiments, be stored in two or more databases, or may be dynamically generated rather than stored. In the illustrated embodiment, the data stored in database 214 is referred to as "attribute information." This term means that the database contains values that represent information about various attributes of drugs. The term "target-reference data" refers to a particular subset of this attribute information, that is, to attribute information regarding selected target and reference drugs. As will be evident to those skilled in the relevant art, database 214 may, rather than storing attribute data directly, alternatively store indirect references to data such as by storing pointers to locations at which are stored the data, or other pointers-to-pointers to data, and so on.

Figure 5:
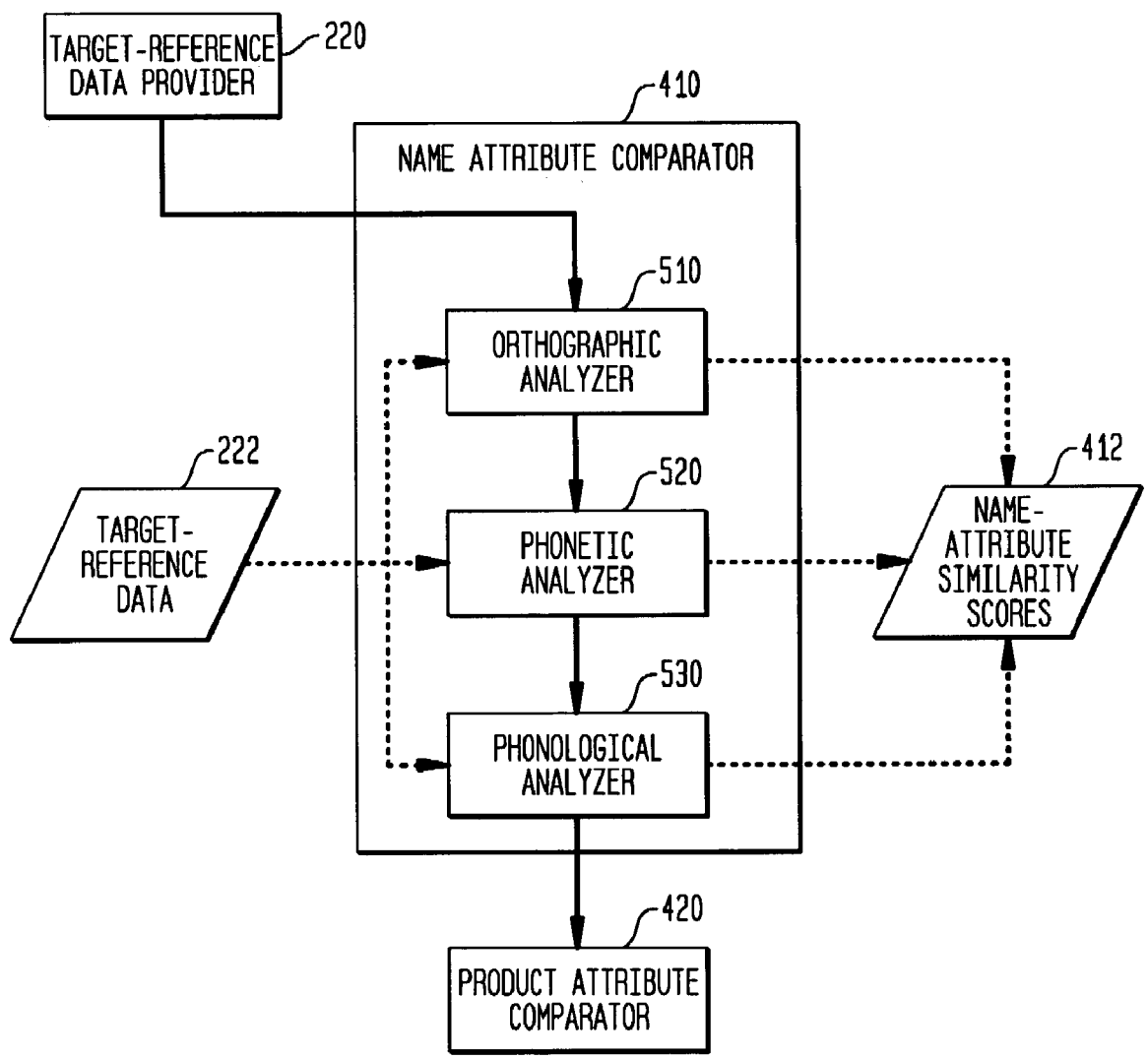
FIG. 5 is a functional block diagram of one embodiment of a name attribute comparator of the attribute similarity scores generator of FIG. 4.
Figure 6:
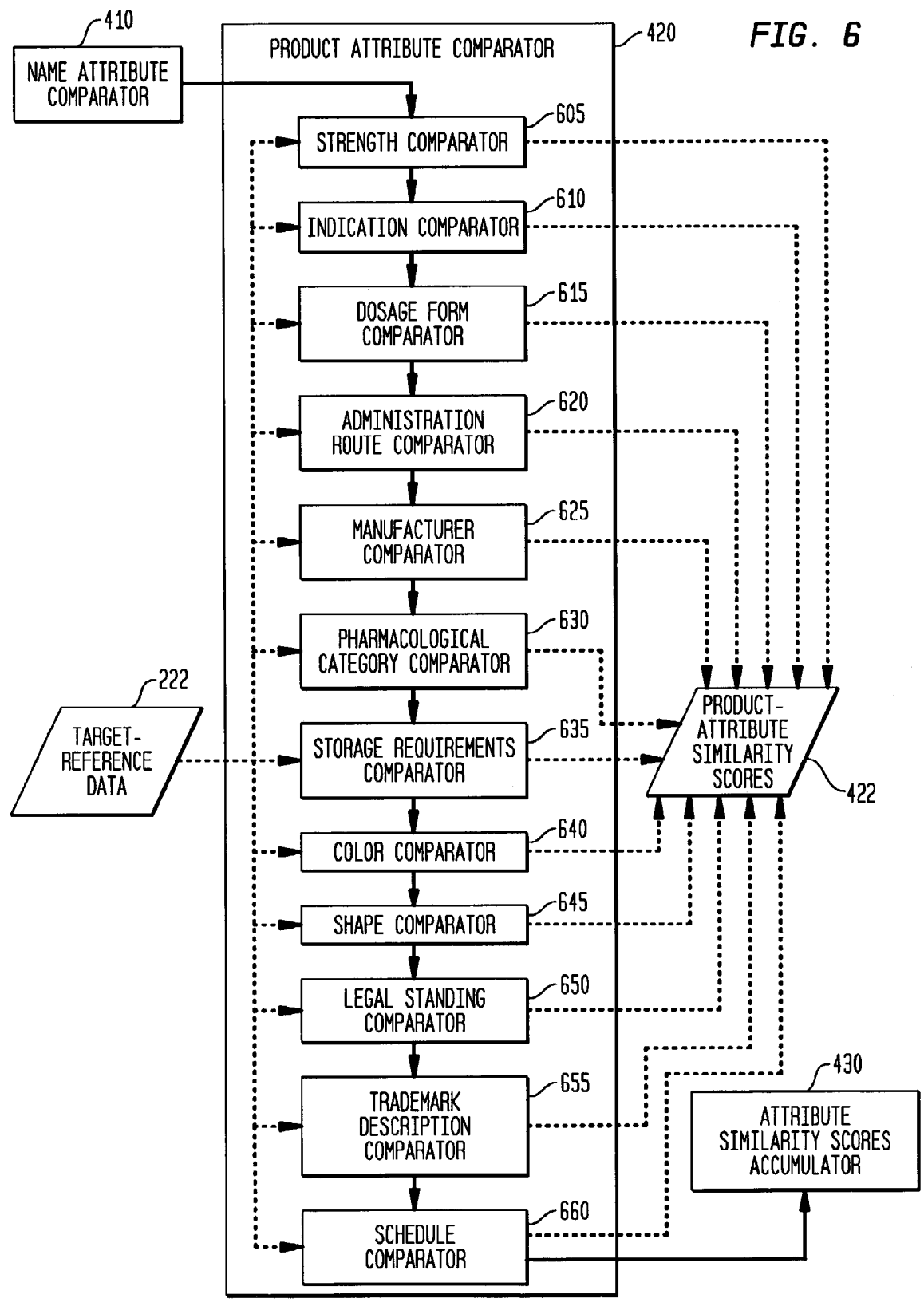
FIG. 6 is a functional block diagram of one embodiment of a product attribute comparator of the attribute similarity scores generator of FIG. 4.

One of many possible embodiments of database 214 is shown in FIG. 2B. The horizontal rows of database 214 of FIG. 2B may be referred to as records. There is a record in this embodiment for each drug having attributes described in database 214. The left-most column provides record numbers for convenience of reference only, and will be understood not to represent part of database 214. The vertical columns of database 214 indicate various fields of those records. Fields in the first column of this illustrative embodiment, column 214A, contain values that provide a unique identifier for each drug. Fields in columns 214B, 214C, 214D, and 214N respectively contain values that describe the name, color, strength, and trademark description attributes of the drugs identified in column 214A. The label 214N is intended to indicate that any integer number N of attributes may be contained in database 214. That is, the attributes shown and described herein, such as with respect to FIGS. 2B, 5 and 6 are intended to be illustrative only, and not limiting. It is not required that there be a value for each attribute for each drug; e.g., it is not required that a value be provided for every field of every record.

For illustrative purposes, it may be assumed that database 214 is initialized so that it contains no data. Attribute information may be stored in initialized database 214 in any of a variety of known ways. For example, as shown in FIG. 1, local update information 172 may be entered through any of a variety of possible input devices of input-output devices 160. For example, drug identifies and drug attributes may be stored on a diskette so that this information may be read by use of a disk drive and then an image of this data stored in memory 130. As is evident, this information may also be entered using a keyboard, or any of a number of other devices or techniques. Also, the same, or additional, information may be provided from a remote source, such as a network server (not shown) connected through the Internet or another network (not shown) to a local server (not shown) and thence to user computer 110 through its network interface 140. A local area network or intranet may also be used. This remote information is represented in FIG. 1 by remote update information 174. The images in memory 130 of local update information 172 and/or remote update information 174 are represented in FIG. 2A by local and remote update information 212.

In accordance with any of a variety of known techniques, such as sort and store techniques, attribute database updater 210 stores information 212 in database 214. Thus, it may be assumed for illustrative purposes that local update information 172 includes attribute information regarding the drugs Ambien® and Amen®, and that remote update information 174 includes attribute information regarding the drug Zantac®. It is further assumed that, in accordance with known techniques, images of this attribute information are stored as local and remote update information 212 in memory 130. Updater 210 then assigns a unique identifier to each drug, which may be done in accordance with any of a variety of known techniques. Also, updater 210 of the illustrated embodiment stores each attribute of each drug in a field of a record corresponding to the associated drug. Thus, for purposes of illustration, the attribute information for Ambient® in 5 milligram tablets is shown in FIG. 2B in record 1 of database 214, including a unique identifier (arbitrarily assumed to be "00001" in this example) that is stored by updater 210 in field 214A-1 of record 1.

As the preceding example indicates, updater 210 of this illustrative embodiment generates a separate record in database 214 for each different combination of attributes of a particular drug. For example, if Ambien® is manufactured in two strengths, such as tablets of 5 milligrams and 10 milligrams, then two records are generated. If each of the two strengths comes in tablets (or other dosage forms) of two colors, then four records may be generated, and so on for any attributes in which alternative values are indicated in local and remote update information 212. As will be evident to those skilled in the relevant art, a variety of other techniques may be used in alternative embodiments to store alternative values of attributes of a drug, such as providing links from a single drug record in one database to alternative field values in other databases.

In addition to adding new records to database 214 for drugs that may be added from time to time to the database, updater 210 may change the values in one or more fields of one or more existing records to update the information contained therein. For example, local update information 172 may be provided to user computer 110 subsequent to the initial generation of database 214. Information 172 at that time may indicate that Ambien® 5 milligram tablets are now pink rather than salmon-colored. Using any of a variety of known techniques, such as search and compare techniques, updater 210 would then modify the value in field 214C-1 to indicate this change in color. In the illustrative example of FIG. 2B, attribute information is shown as text strings, such as "salmon." As will be evident to those skilled in the relevant art, this information may be coded in any of many ways in alternative embodiments so that, for example, field 214C-1 contains a numerical value to represent the color "salmon."

TARGET-REFERENCE DATA PROVIDER 220

As noted, drug comparator 100 in the illustrated embodiment also includes target-reference data provider 220 that provides target-reference data for selected target and reference drugs. In one typical implementation, shown in FIG. 1, a user 102 makes the selections of target and reference drugs. User 102 may be a human being or a machine. This selection is represented in FIG. 1 by a data flow line labeled "user selection 103" that is directed from user 102 to a data object labeled "selected target and reference drugs 104" to indicate that the latter is generated by user 102.

The selection of target and reference drugs may take place in accordance with any of a variety of known techniques. For example, user 102 may be a person who employs a mouse or other input device of input-output devices 160 to select one or more target drugs from a graphical user interface that displays a list of the drug names stored in fields 214B of database 214. User 102 may similarly select one or more reference drugs from the list, or may otherwise indicate that all, or a range of, drugs on the list are to be used as reference drugs. Generally, as noted above, one or more target drugs may be compared to one or more reference drugs in one-to-one, one-to-many, many-to-one, or many-to-many relationships. In the illustrated embodiment, it is assumed for convenience, unless otherwise indicated, that user 102 selects the target and reference drugs so that the comparisons are made on a one-to-one basis. That is, for example, one target-reference pair of drugs A and B are compared, then another target-reference pair of drugs A and C are compared, and so on. As will be described below in relation to the operations of confusability score generator 325, user 102 may make other selections of target and reference drugs (e.g., selected target and reference drugs 215B of FIG. 8) related to determining a target confusability score for a target drug in comparison to a set of reference drugs in the "neighborhood" of the target drug.

In a known manner, an image of the names, and/or other identifiers, of selected target and reference drugs 104 may be stored in memory 130 for processing by drug comparator 100. For example, in the illustrated embodiment, this image is shown as selected target and reference drugs 215A in FIG. 2A.

In some embodiments, the present invention may be directed to a method for comparing target and reference drugs, a storage medium containing software that performs a method for comparing target and reference drugs, or a product including a comparison of target and reference drugs generated by a method. For convenience, these embodiments may hereafter be referred to simply as "embodiments involving method steps." FIG. 10 is a simplified flow diagram of one exemplary embodiment involving method steps. It will be understood that the control flow between method steps shown in FIG. 10 is illustrative only, and that many other orders of control flow, including parallel control flow (i.e., carrying out of two or more steps in parallel), are possible. Also, there are many other variations by which any one or more of steps 1010 through 1080 of FIG. 10 may be combined, subdivided, redistributed among other steps, and otherwise rearranged.

In embodiments involving method steps, the operations of target-reference data provider 220 generally are carried out in a method step illustratively represented by step 1010 of FIG. 10. That is, a target-reference pair including at least one target drug and at least one reference drug are identified. As shown by FIG. 10, steps 1020 through 1070, described below, are then taken and it is determined (in step 1080) whether it is desired to compare another target-reference pair. If so, then step 1010 is again invoked so that this new target-reference pair is identified for further processing. It will be understood that, in alternative embodiments involving method steps, all target-reference pairs may be identified before any of them are processed, or they may be identified and processed in batches (e.g., 100 target-reference pairs may be processed in accordance with steps 1010 through 1080, then another 100 target-reference pairs may be so processed, and so on).

Returning now to the embodiment of drug comparator 100 illustrated in FIG. 2A, target-reference data provider 220 uses selected target and reference drugs 215A to select appropriate target-reference data from drug attribute database 214. This operation may be accomplished in accordance with any of a variety of known techniques, such as compare and search techniques. Target-reference data provider 220 then stores this selected information in a data object referred to in the illustrated embodiment as target-reference data 222. (With respect to embodiments involving method steps, these operations generally are represented by step 1020 of FIG. 10.) For example, it may be assumed that user 102 selects Amen® to be the target drug and Zantac® to be the reference drug so that composite analyzer 230 may generate a comparison of this target-reference pair. Target-reference data provider 220 thus, in one illustrative implementation, copies the records in database 214 corresponding to those two drugs (the third and M'th records, respectively) to similarly structured records in target-reference data 222. FIG. 2C is a simplified schematic representation of data 222 for this illustrative example. It will be understood that target-reference data 222 is shown as a separate data structure from drug attribute database 214 for convenience and clarity of illustration only. As will be evident to one skilled in the relevant art, flags or other techniques may alternatively be used to mark or otherwise identify selected records in database 214 for processing, rather than replicating information in a new data object such as target-reference data 222.

In some implementations, target-reference data provider 220 may process the values of the product attributes in fields 222A through 222N of target-reference data 222. (In other implementations, this processing may be done by attribute database updater 210 when it generates or updates drug attribute database 214 and/or by name attribute comparator 410 or product attribute comparator 420 as described below.) More specifically, the values of the name and/or product attributes may be processed to facilitate comparisons among them. For example, and as described in greater detail below in relation to the operations of product attribute comparator 420, the color attribute "white" in field 222C-3 may be processed so that this text string is converted to a numerical value. Various known techniques, or ones to be developed in the future, may be applied to compare colors expressed as numerical values to generate a quantitative measure of the similarity between the colors. In other implementations, unprocessed attribute values, e.g., text strings, may be compared to generate a quantitative measure of similarity.

In any of these implementations, the value of a name or product attribute of a target and/or a reference drug may be envisioned for illustrative purposes as a value along an axis that represents possible values of that attribute. Other representational approaches include the use of graphs having nodes separated by certain distances, in which topological measures of similarity could be employed. Another approach would be to determine a hamming distance between members of a set. More generally, any mathematical representation could be used for representing values of attributes and determining a distance measurement that is related to a similarity between or among attributes. Also, any of a variety of known pattern-matching techniques could be used to determine associations, or to otherwise measure correlations, between or among attributes. With respect to the illustrative representation using axes, if the target and reference drugs have N attributes, as illustratively shown in FIGS. 2B and 2C, then N axes may be used, having either discrete or continuous values, where each axis corresponds to one of the name or product attributes. Thus, an N-dimensional space may be defined in which positions may be determined for the target and reference drugs (or any other drug in database 214) that respectively represent the values of the attributes of those drugs.

Figure 2D:
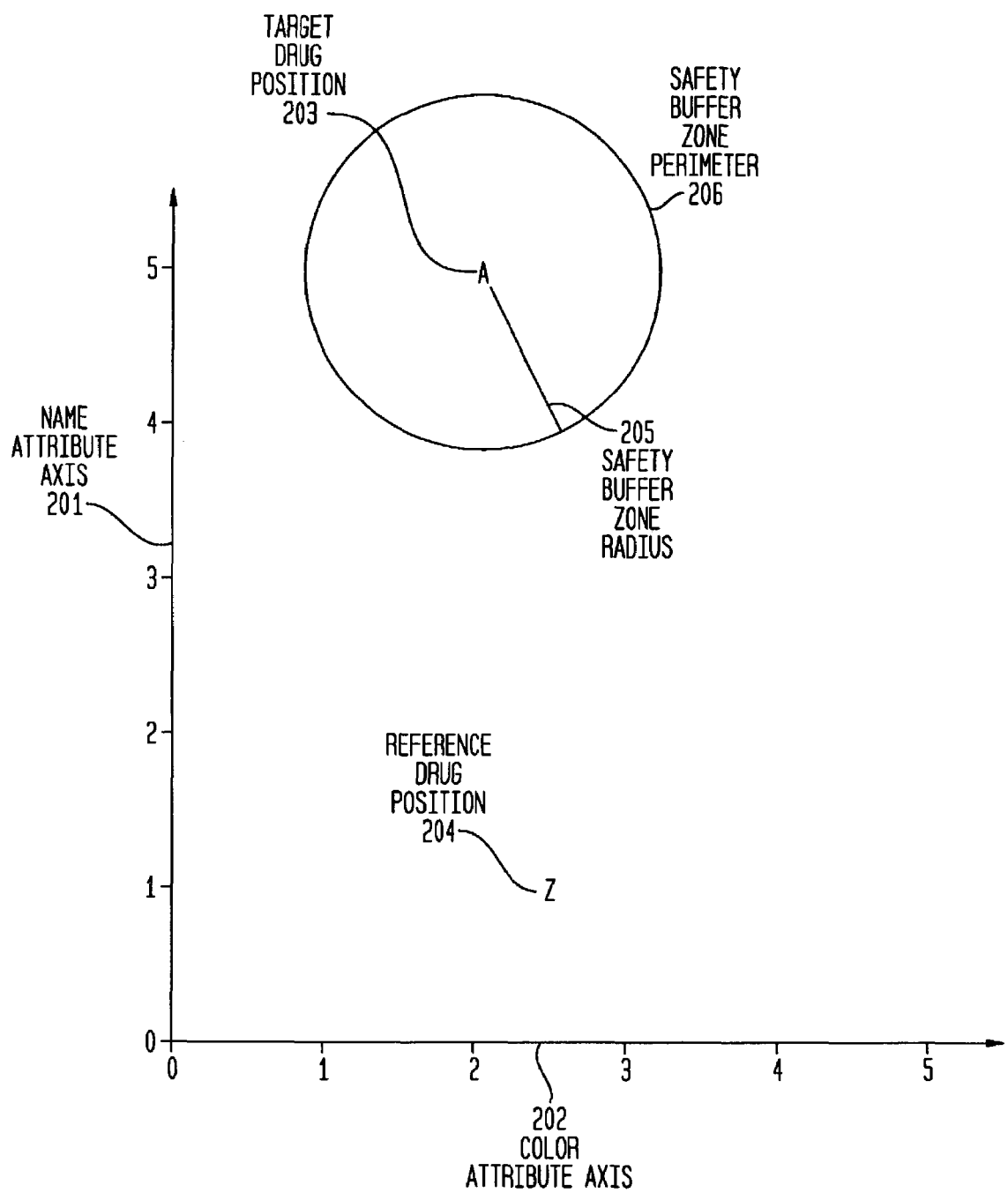
FIG. 2D is a graphical representation of one embodiment of an illustrative 2-dimensional attribute space, showing positions of a target drug and a reference drug based on an exemplary embodiment of the target-reference data of FIG. 2C.

For example, FIG. 2D is one embodiment of a graphical representation of an illustrative 2-dimensional attribute space in which horizontal axis 202 represents values of color attribute data and vertical axis 201 represents values of name attribute data. Although these axes are shown for convenience as having generally equal value dimensions, it need not be so. Also, any of a variety of known alternative types of scales, such as a logarithmic scale, may be used. FIG. 2D shows positions of exemplary target and reference drugs in the illustrative 2-dimensional space. The attributes of the target and reference drugs are illustratively assumed to be those stored respectively in records 3 and M of target-reference data 222, which respectively contain values of attributes of the drugs Amen® and Zantac®. It has been assumed that the name-attribute values "Amen" and "Zantac" have been processed so that they are respectively represented by the numerical values 5.0 and 1.0. It has similarly been assumed that the corresponding color-attribute values "white" and "yellow" are represented by the numerical values 2.0 and 2.5.

In some embodiments, as indicated by data flow line 223 of FIG. 2A, an aspect of composite quantitative comparison 216 may be a graphical or other type of representation of the positions of one or more target-reference pairs. For example, the graphical representation of FIG. 2D may be included in composite quantitative comparison 216. To facilitate interpretation of a graphical representation such as is shown in FIG. 2D, a value such as the illustrative safety buffer zone radius 205 of FIG. 2D may be determined. For example, this radius may be derived from experimental data regarding the likelihood of confusion among drugs based on their names and colors. When centered on target drug position 203, shown with the symbol "A" in FIG. 2D, radius 205 describes a safety buffer zone perimeter 206 that, in the illustrative 2-dimensional space, is a circle. Because reference drug position 204, shown with the symbol "Z," is outside of perimeter 206, this illustrative graphical portion of composite quantitative comparison 216 may readily be interpreted by a user as indicating that the target and reference drugs are not likely to be confused, based on their names and colors. Other reference drugs may similarly be plotted in this 2-dimensional space so that those reference drugs that are within the safety buffer zone (i.e., relatively likely to be confused with the target drug based on name and color attributes) may readily be identified. As is evident, similar graphical representations may be generated that show safety buffer zones consisting of spheres in a 3-dimensional space based on three attributes of target and reference drugs. As also is evident, any combination of attributes may be used.

COMPOSITE ANALYZER 230

Figure 3A:
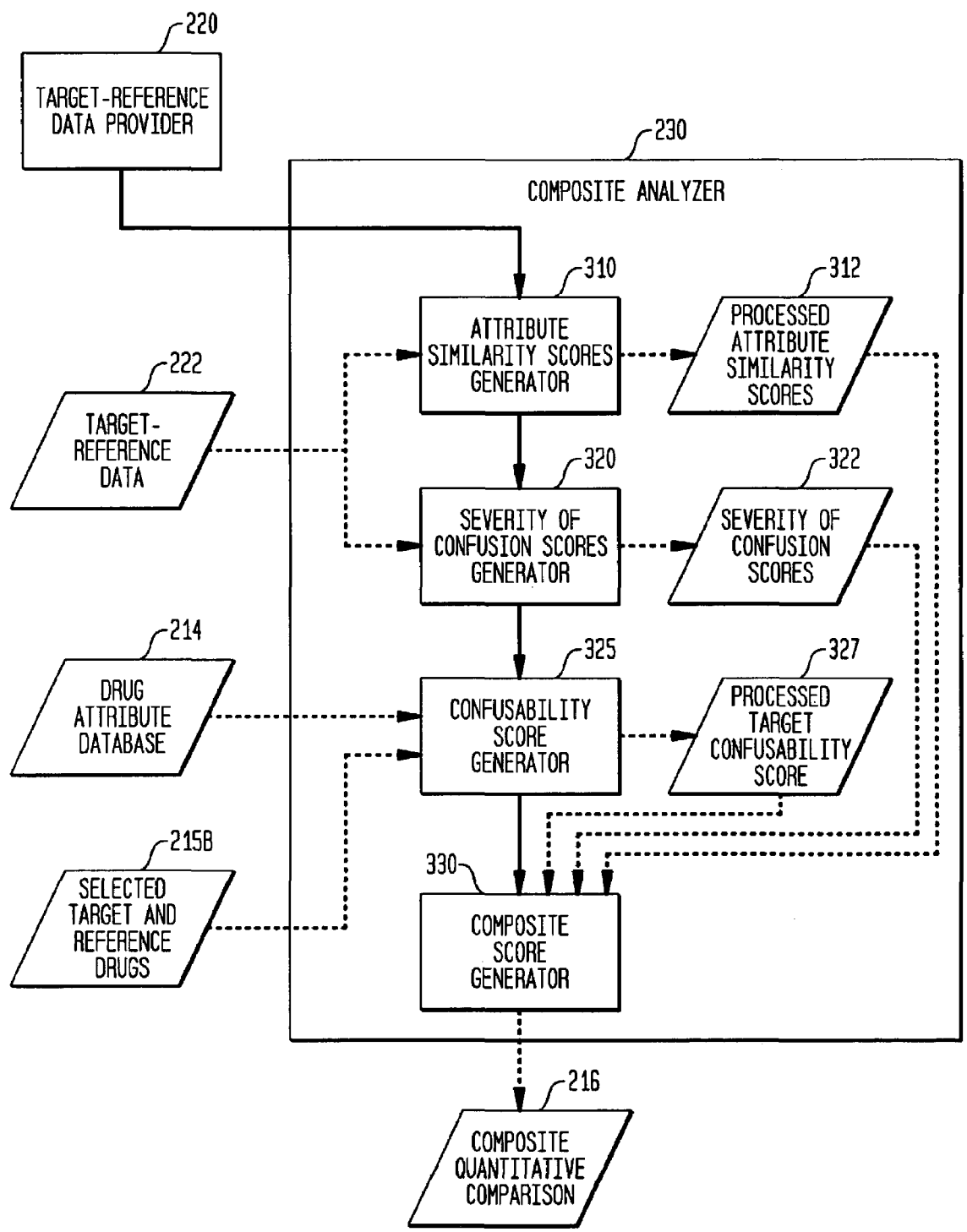
FIG. 3A is a functional block diagram of one embodiment of a composite analyzer of the drug comparator of FIG. 2A.
Figure 3B:
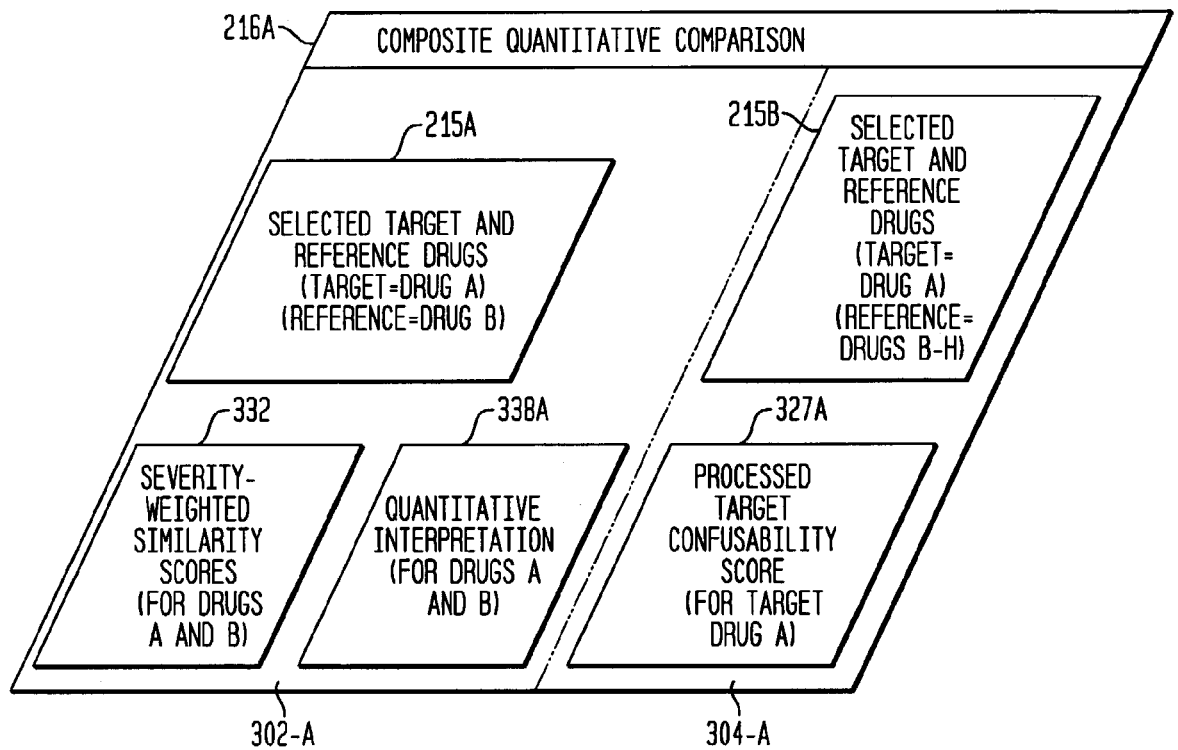
FIG. 3B is a schematic representation of one embodiment of a composite quantitative comparison generated by the composite analyzer of FIG. 3A.
Figure 3C:
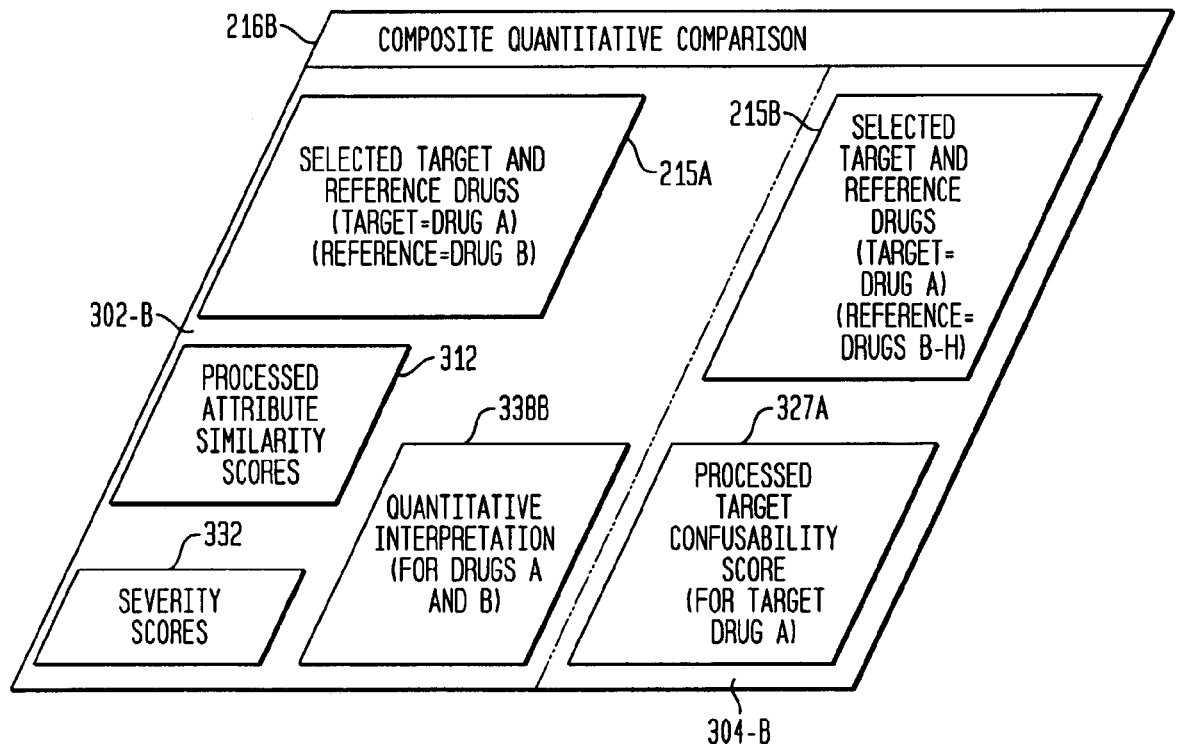
FIG. 3C is a schematic representation of another embodiment of a composite quantitative comparison generated by the composite analyzer of FIG. 3A.

FIG. 3A is a functional block diagram of composite analyzer 230. As shown in FIG. 3A, composite analyzer 230 generates one or more "composite quantitative comparisons" of the selected target and reference drugs based on target-reference data 222. These composite quantitative comparisons are represented for convenience in the illustrated embodiment by the data object labeled "composite quantitative comparison 216." Two of various alternative embodiments of composite quantitative comparisons are schematically shown in FIGS. 3B and 3C. Composite analyzer 230 includes attribute similarity scores generator 310 that generates one or more processed attribute similarity scores 312 representing a similarity of attributes of the selected target and reference drugs. Also included in composite analyzer 230 is severity of confusions score generator 320 that generates one or more severity of confusion scores 322 representing a severity of confusion between the target and reference drugs. Another element of composite analyzer 230 is composite score generator 330 that generates the one or more composite quantitative comparison 216 based, at least in part, on the processed attribute similarity scores 312. Yet another element of composite analyzer 230 is confusability score generator 325 that generates, for each of one or more target drugs, one or more processed target confusability scores 327 representing the confusability of the target drugs. These elements of the illustrated embodiment of composite analyzer 230 are now described in turn.

ATTRIBUTE SIMILARITY SCORES GENERATOR 310

Figure 4:
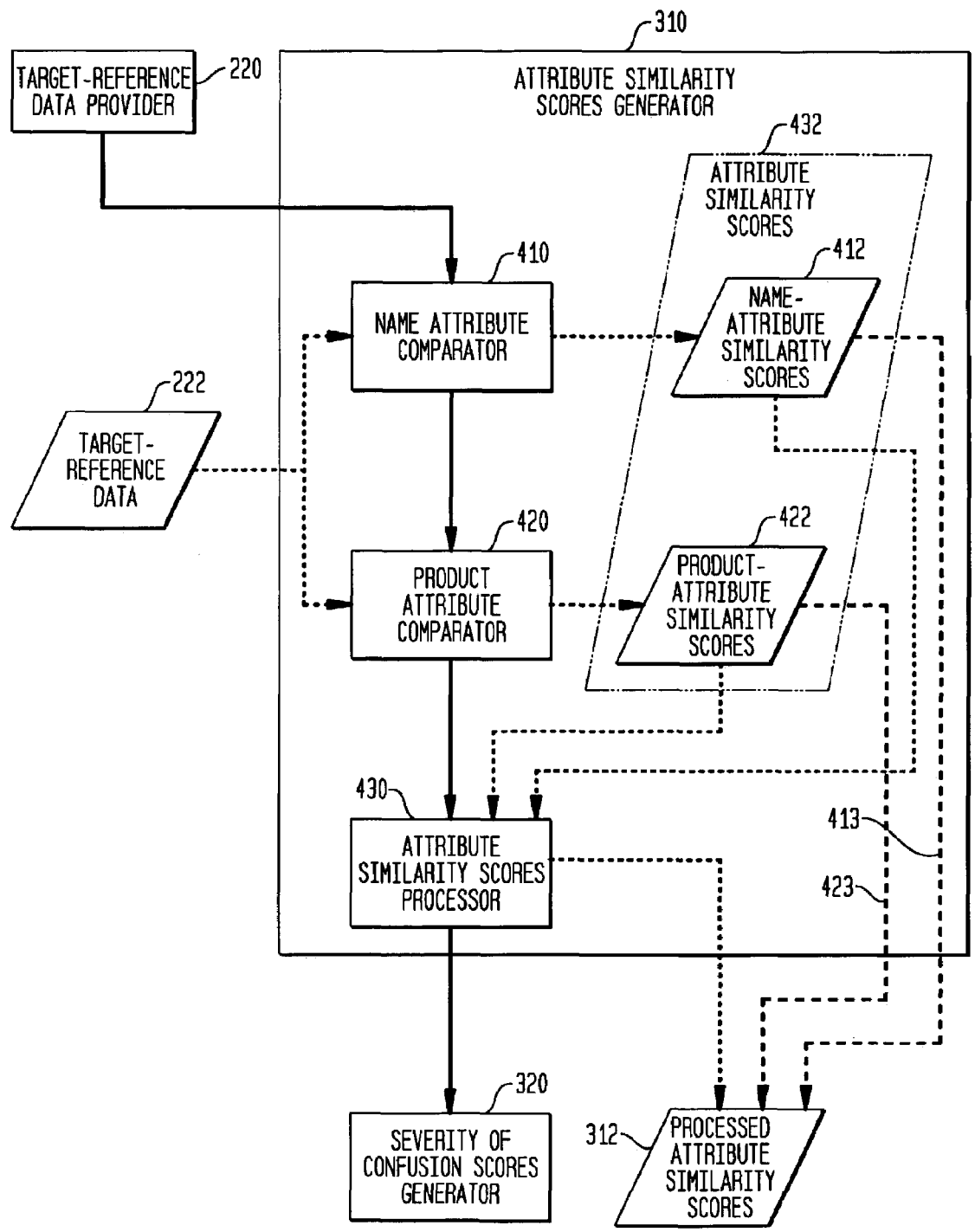
FIG. 4 is a functional block diagram of one embodiment of an attribute similarity scores generator of the composite analyzer of FIG. 3A.

FIG. 4 is a functional block diagram of attribute similarity scores generator 310. As shown in FIG. 4, generator 310 includes name attribute comparator 410, product attribute comparator 420, and attribute similarity scores processor 430. Name attribute comparator 410 generates one or more name-attribute similarity scores 412 representing a similarity of name attributes of the selected target and reference drugs. Name-attribute similarity scores 412 may be generated by comparator 410 based on orthographic, phonetic, and/or phonological measures of the names of the target and reference drugs. Product attribute comparator 420 generates one or more product-attribute similarity scores 422 representing a similarity of product attributes of the selected target and reference drugs. As noted above, many product attributes may be included in target-reference data 222 and thus employed in this comparison. Attribute similarity scores processor 430 may be employed to generate processed attribute similarity scores 312 based on attribute similarity scores 432. This processing may be accomplished in many ways, including simply listing product-attribute similarity scores 312, or weighting and then listing them, as described below. These elements of attribute similarity scores generator 310 are now each described in greater detail.

NAME ATTRIBUTE COMPARATOR 410

FIG. 5 is a functional block diagram of name attribute comparator 410 that includes orthographic analyzer 510, phonetic analyzer 520 and phonological analyzer 530. Each of these analyzers in the illustrated embodiment uses target-reference data 222 as input, and each produces as output a name-attribute similarity score 412. With respect to embodiments involving method steps, these operations of name attribute comparator 410 generally are represented by step 1030 labeled "generate name-attribute similarity scores."

For purposes of illustration, the previous example is again employed in which user 102 has selected Amen® as the target drug and Zantac® as the reference drug. Thus, as shown in FIG. 2C and described above with respect to the operations of target-reference data provider 220, target-reference data 222 contains attribute information about target drug Amen® in record 1 and attribute information about reference drug Zantac® in record 2. Each of the analyzers operates specifically on the name-attribute information in these records; that is, in this example, they operate on name-attribute field 222B-3 for the target drug and name-attribute field 222B-M for the reference drug.

As previously noted, a drug may have a number of different name attributes, such as a generic name, a proprietary brand name, a non-proprietary name, or an abbreviation. In some embodiments, a separate record may be generated in drug attribute database 214 and/or target-reference data 222 for each variation in name attribute, or any of a variety of other known schemes for organizing data may be used. Thus, for example, record 3 in drug attribute database 214 may be only one of a number of records in that database pertaining to the drug having the proprietary brand name Amen®. Another record may be generated that has the same attribute information as record 3, except that the chemical name of that drug, medroxyprogesterone acetate, is used in the name attribute field. Similarly, one record may be generated in database 214 in which the name attribute field contains the non-proprietary name "aspirin," and a second record may be generated in which the name attribute field contains a common abbreviation for aspirin, "ASA." The attributes in this second record for aspirin may be compared, for example, with the attributes in another record for the drug mesalamine, which has the abbreviation "5-ASA."

Orthographic analyzer 510. Orthographic analyzer 510 generates one or more name-attribute similarity scores 412 based at least in part on one or more comparisons between orthographic representations of the names of the selected target and reference drugs. An orthographic representation is one that represents the similarity in spelling of words. There are many known techniques for representing the orthographic qualities of words and for measuring the similarity between the orthographic representations. These techniques are hereafter referred to for convenience simply as "orthographic measures." They have been applied in a variety of fields. See, for example, the approaches and applications described in G. A. Stephen, *String Searching Algorithms*, (World Scientific, River Edge, N.J.; 1994); J. Aoe, *Computer algorithms: String pattern matching strategies*,(IEEE Computer Society Press, Washington, D.C.; 1994); S. F. Altschul, W. Gish, W. Miller, E. W. Myers, and D. J. Lipman, "Basic local alignment search tool," in *Journal of Molecular Biology*, vol. 215, pp. 403–410 (1990). Any of these or other known orthographic measures, orthographic measures that may be developed in the future, or any combination thereof, may be used by orthographic analyzer 510.

For example, one known type of orthographic measure is often referred to as an "N-gram measure," which refers to the breaking up of target and reference words into sequences of n-letters and then computing a similarity measure based, at least in part, on the number of these n-letter sequences that the two words have in common. There are a variety of known N-gram measures, such as bigram and trigram measures (using two-letter and three-letter sequences, respectively). For example, the target drug Acthar® may, using a bigram measure, be broken up into the sequences "ac," "ct," "th," "ha," and "ar." The reference drug Acular® yields the bigram sequences "ac," "cu," "ul," "la," and "ar." Any of a number of known statistical approaches may then be used to make the comparison, such as by computing an orthographic similarity measure equal to a ratio in which the numerator is twice the number of bigrams that are common to both names, and the denominator is the sum of the number of bigrams in both words. The bigram measure of similarity between these two drug names thus is, using this illustrative statistical calculation, 2*2/ (5+5)=0.4. Variations of this approach are known, as, for example, increasing the sensitivity of the measure to the beginnings and endings of words by adding a space at those places. For example, Acthar® would, in this variation, also include the bigram sequence "a" (space, "a"), and Acular® would also include "a" (space, "a"). The commonality of these two words would then increase by one, even though the sequence "ac" is also counted as being common, thus doubling the impact of the commonality of initial letters.

Another type of known orthographic measure is often referred to as an "edit distance measure." The term "edit distance" refers to the number of edits, i.e., insertions, deletions, or substitutions, needed to transform one word into another. For example, to transform Ambien® into Amen®, two deletions are necessary. Thus, the edit distance between these words is 2. This distance, using one of a variety of possible variations, may be "normalized" by dividing it by the maximum possible edit distance between the two words, which is the length of the longer of the two words. Using the example of transforming Ambien® into Amen®, the normalized edit distance thus is 2 divided by 6.

Phonetic analyzer 520. Phonetic analyzer 520 generates one or more of name-attribute similarity scores 412 based at least in part on one or more phonetic measures of the names of the selected target and reference drugs. As noted, the term "phonetic measure" is used for convenience herein to mean that phonetic transformation has been applied and that a measure of orthographic similarity has been made of the phonetically transformed representation. For example, the drug Xanax® may be phonetically transformed to the word "Zanex," because the initial "X" is pronounced as a "Z." Then, to obtain a "phonetic measure" of the similarity of Xanax® and, for example, Zantac®, an N-gram or edit distance technique may be applied to the words "Zanex" and "Zantac." Generally, therefore, the term "phonetic measure"

is used herein to refer to a measure of the similarity in sound patterns of words. More specifically, a phonetic measure generally involves transforming the orthographic representation of a word (which could be the target drug name, the reference drug name, or both) into a representation that is intended to capture regularities in sound patterns of the language in which the word is written, and then determining a measure of the orthographic similarity of the transformed word (or words). The resulting measure is sometimes referred to as indicating the "phonetic distance" between the words being compared. Some information on known techniques for determining phonetic distance is provided in J. Zobel and P. Dart, "Phonetic string matching: Lessons from information retrieval," in H. P. Frei, D. Harman, P. Schauble, and R. Wilkinson (eds.), *SIGI96: Proceedings of the 19th Annual International ACM SIGIR Conference on Research and Development in Information Retrieval*; August 1996 18–22: Zurich, Switzerland (Association for Computing Machinery, New York; 1996), pages 166–172. Some non-limiting examples of phonetic distance approaches that will be familiar to those skilled in the relevant art are "soundex," "phonix," "editex," "tapered edit distance," "omission key," and "skeleton key."

With respect to the operations of phonetic analyzer 520, phonetic measures may be employed using known, or to be developed, techniques that take into account variations in the pronunciation of words and thus are not limited to the sounds of words based on their written form. For example, mistakes may occur because a prescription is filled based on an oral communication in which any number of factors, such as regional dialects, personal diction, emotional stress, nonstandard pronunciations, or noise in the communication channel, modify the sound patterns of drug names. Any of these or other known phonetic measures, phonetic measures that may be developed in the future, or any combination thereof, may be used by phonetic analyzer 520.

Phonological analyzer 530. Phonological analyzer 530 generates one or more name-attribute similarity scores 412 based at least in part on one or more phonological measures of the names of the target and reference drugs. A phonological measure is one that measures not just the linguistic similarities of words (as do orthographic and phonetic measures), but also the likelihood of confusion due to cognitive processing of the phonological features of words. Phonological features include properties of the sound pattern of words that have known and/or measurable impact on mental representations and processes. Psychologists, linguists, and other cognitive scientists have studied in some detail the mechanisms by which such cognitive processes as memory and perception can influence a person's propensity to confuse one word with another.

There are many relevant aspects to each of these processes. For example, distinct psychological effects have been noted with respect to whether the memory involved is short-term as opposed to long-term, and analogous distinctions may be drawn with respect to recall and recognition. With respect to perception, distinctions may be based on the various modalities that may be involved (e.g., visual or auditory), the communication media involved (e.g., handwriting, typewriting, facsimile, computer monitor, telephone, direct oral communication), and/or the type of stimuli degradation encountered (e.g., homogeneous or inhomogeneous noise). Also, the ways in which the human brain forms and responds to associations among stimuli are complex and highly relevant to both memory and perception. Some of these mechanisms are noted in B. L. Lambert, "Predicting look-alike and sound-alike medication errors," in *American Journal of Health-System Pharmacy*, vol. 54, pp. 1161–71 (1997), the entirety of which is hereby incorporated by reference. Some known phonological measures are discussed in A. D. Baddeley, *Working Memory* (Oxford University Press, Oxford; 1986); B. L. Lambert, et al., "Effect of similarity on pharmacists' recall and recognition of drug names," in *PharmSci,* 1998, vol. 1, page 1333; P. A. Luce, et al., "Similarity neighborhoods of spoken words," in G. T. M. Altmann (ed.), *Cognitive models of speech processing: Psycholinguistic and computational perspectives* (MIT Press, Cambridge, Mass.; 1990) at pp. 122–47.

For example, Premarin® is one of the most frequently prescribed drugs in the world. The drug Primaxin® is relatively rarely prescribed. Cases have been reported in which Premarin® was dispensed when Primaxin® was intended. In part, this confusion may be due to the orthographic and phonetic similarities of these names. However, there is evidence that these are not the only effects involved. If they were the only, or even predominant, effects, it generally would be expected that there would be a roughly equal rate of confusion of Premarin® for Primaxin® as there is confusion of Primaxin® for Premarin®. However, the dispensing of Primaxin® when Premarin® was intended has not been observed to be a significant problem. This asymmetry can be explained by what psycholinguists often refer to as the "word frequency effect." Aspects of this and related effects are discussed in A. Garnham, *Psycholinguistics: Central Topics*, Methuen, N.Y. (1987); R. L. Solomon and L. Postman, "Frequency of usage as a determinant of recognition threshold for words," in *Journal of Experimental Psychology*, vol. 43, pp. 195–210 (1952); J. Grainger, et al., "On the role of competing word units in visual word recognition: The neighborhood frequency effect," in *Perception and Psychophysics* vol. 45, pp. 189–195 (1989); J. Grainger, "Word frequency and neighborhood frequency effects in lexical decision and naming," in *Journal of Memory and Language*, vol. 29, pp. 228–244 (1990). Generally speaking, the word frequency effects refers to the cognitive tendency to more readily perceive and remember frequently encountered words than infrequently encountered words. Another known cognitive effect that appears to be related to the word frequency effect is referred to in the literature as the "neighborhood frequency effect." Generally speaking, the neighborhood frequency effect is the tendency of infrequently encountered words to be confused with more frequently encountered words that are similar. This effect appears to become more important as the stimulus (e.g., the handwritten name of a drug on a prescription) is degraded (e.g., by poor handwriting). Various techniques are known for providing phonological measures of similarity among words, and any of these known techniques, other phonological measures that may be developed in the future, or any combinations thereof, may be employed by phonological analyzer 530.

PRODUCT ATTRIBUTE COMPARATOR 420

As noted, product attribute comparator 420 generates one or more product-attribute similarity scores 422 representing a similarity of product attributes of the selected target and reference drugs. FIG. 6 is a functional block diagram of product attribute comparator 420. As shown in FIG. 6, product attribute comparator includes comparators 605–660, each one of which is related to a product attribute. In the illustrated embodiment, each of these constituent comparators uses target-reference data 222 as input and generates as output one or more product-attribute similarity scores 422.

With respect to embodiments involving method steps, these operations of product attribute comparator 420 generally are represented by step 1040 labeled "generate product-attribute similarity scores."

It will be understood that, as with respect to analyzers 510–530 of comparator 410, control flow among comparators 605–660 need not be as indicated in this illustrative embodiment. Rather, in alternative embodiments, any sequence of control flow among comparators 605–660 may be used, they may be processed in parallel, or combinations of serial and parallel processing may be used. Also, it will be understood that comparators 605–660 are illustrative only and non-limiting. In alternative embodiments, other and/or additional comparators may similarly be employed based on other and/or additional product attributes.

Comparators 605–660. Comparators 605–660 each compare a product attribute of the one or more target drugs with the corresponding product attribute of the one or more reference drugs, as described in greater detail below. With respect to each of comparators 605–660, any of a variety of known techniques, or techniques to be developed in the future, may be used to provide a quantitative measure of the corresponding product attributes. That is, any known or future technique may be applied by each of the comparators to the information in target-reference data 222 to provide a value for corresponding product attributes of the target and reference drugs so that a quantitative comparison may be made.

For example, a number may be assigned to each known or anticipated value of an attribute, and a dichotomous product attribute similarity score (e.g., 1 or 0) may be generated based on whether the value of the target drug's attribute matches or does not match the value of the reference drug's corresponding attribute. Many variations of this approach are possible, such as normalizing the score by taking into account the number of possible values that an attribute may have. Many other approaches may also be used, such as applying formulas such that if the value of the target drug's attribute (for example, the color gray, represented by the value 3) is close to the value of the reference drug's corresponding attribute (for example, the color white, represented by the value 1), then product attribute similarity score 422 is greater than would be the case if the reference drug's corresponding attribute had been more remote (for example, the color red, represented by the value 9).

Thus, in general, at least two functions may be carried out by each of comparators 605–660. One function is to convert a product attribute to a form that is suitable for comparison. However, in some implementations, this function may have been done by target-reference data provider 220, or another element of drug comparator 100, so that the product attribute information in target-reference data 222 is already in a form suitable for comparison. The type of form that is suitable for comparison generally depends on the technique for making the comparison. For example, if the comparison is one that compares text strings, then the values of the product attributes being compared should be in the form of text. If the comparison is one that applies a mathematical formula, it generally is advantageous if the values of the product attributes being compared are in the form of numbers. As noted, comparisons may also be accomplished using sets or graphs to represent values of attributes.

Another function generally carried out by each of comparators 605–660 is to apply a comparison technique to the values of the product attributes of the target and reference drugs in order to generate a quantitative value, i.e., a product-attribute similarity score 422, representative of the similarity between the values of the product attributes being compared. For example, if the comparison is between text strings, then edit distance, N-gram, or other known of future techniques for comparing strings of characters may be used. If the comparison is between numbers, then any of a variety of known or future techniques for generating a quantitative measure of the similarity between numerically expressed values may be employed. Some known comparison techniques are described in T. Kohonen, *Content-Addressable Memories*, Springer-Verlag, Berlin (2d. ed., 1987), section 1.4.2 ("Similarity Measures") at pages 19–27, this portion of which hereby is incorporated herein by reference. Among the similarity measures described in Kohonen, all of which are well known by those skilled in the relevant art, are hamming distance, direction cosines, measures of similarity in the Minkowski metric, the Tanimoto similarity measure, weighted measures for similarity, comparison by operations of continuous-valued logic, variational similarity, dynamic matching procedures, edit distance (also referred to as Levenshtein distance), and similarity by invariant features. Any of these techniques, and/or variations or combinations thereof, may be used by any of comparators 605–660, and/or by other comparators related to other product attributes that may be included in product attribute comparator 420 in alternative embodiments.

The type of comparison technique used generally will depend on the nature of the product attribute information being compared. For example, a comparison of key words in a trademark description, as described below with respect to trademark description comparator 655, often will involve comparisons of characters rather than a comparison between numbers. In contrast, a comparison of dosage strengths, as described below with respect to strength comparator 605, often will involve comparisons of numbers and units rather than a comparison between characters. However, many variations are possible. For example, it may illustratively be assumed that there are 12 recognized types of "legal standing" that may be entered in drug attribute database 214 to describe the legal standing of a drug. These 12 types may be entered in database 214, and retained in target-reference data 222, as character strings, thus enabling legal standing comparator 650 dichotomously to quantify a comparison between the legal standing attributes of a target drug and a reference drug; e.g., as noted above, to generate a value of 1 if they match or 0 if they do not. In one of various alternatives, a numerical value may be assigned to each of the 12 recognized types of legal standing in a manner so that similar types have numbers that are close to each other and dissimilar types have numbers that are far from each other. This assignment, referred to for convenience hereafter as "coding," and grammatical variants thereof, may be done by a user who enters data into database 214, by target-reference data provider 220, by comparator 650, or by another element of drug comparator 100. The coding may be accomplished using any of a variety of known techniques, such as using a look-up table (not shown) that correlates character strings with numerical values. After a numerical value is coded for the character string, any technique for quantifying distance between numbers may be used by legal standing comparator 645 to generate a quantitative measure of the similarity of the legal standing attributes of the target and reference drugs.

Various product attributes, for example, strength and dosage form, may be correlated with each other. For example, a dosage strength of 5 milligrams for a particular drug may be correlated with a tablet dosage form, whereas a 10 milligram strength of the same drug may be correlated with a capsule dosage form. In cases where this illustrative strength-form correlation occurs, the strengths of target and reference drugs may be compared by strength comparator 605 to generate a product-attribute similarity score 422 based solely on strength, dosage forms of the same target and reference drugs may be compared by dosage form comparator 615 to generate a product-attribute similarity score 422 based solely on dosage form, and either of these comparators may generate an additional product-attribute similarity score 422 based on a composite function of the similarities of both the strengths and the dosage forms of the target and reference drugs. For instance, the score may be the sum, or any other statistical measure, of the score based on strength and the score based on dosage form.

Strength comparator 605. Strength comparator 605 generates one or more product-attribute similarity scores 422 based at least in part on one or more dosage strengths of the target and reference drugs. More specifically, in the illustrative embodiment, comparator 605 compares the strength attributes of the target and reference drugs to generate one or more scores 422. Using the example in which user 102 has selected Amen® as the target drug and Zantac® as the reference drug, strength comparator 605 would therefore compare the values in fields 222D-3 and 222D-M, i.e., it would compare the value 10 milligrams with the value 300 milligrams. As noted, there are many ways in which this comparison could be made and quantified. For example, a string match algorithm could be used, which, in this example, would yield a non-match that could be represented by a product-attribute similarity score 422 of 0.0. As another example, the numerical value 10 could be compared to the numerical value 300 to yield a score that reflected the difference (e.g., a Euclidean or non-Euclidean measure of distance) between these two values.

Indication comparator 610. Indication comparator 610 generates one or more product-attribute similarity scores 422 based at least in part on one or more indicated uses of the target and reference drugs. For example, the "indication attribute" for a drug may have a value that is the text string "antihypertensive," indicating that the use of the drug is to reduce hypertension. As noted, one of many schemes by which these values may be coded and compared is to employ a look-up table (not shown) of standard drug indications in which each indication is associated with a numerical value. This look-up table may be used to provide the values for the appropriate fields (i.e., the indication attribute field) in drug attribute database 214, or text or other strings in the appropriate fields of database 214 may be compared to the entries in the look-up table. In either case, it may illustratively be assumed that a numerical value of 12 is associated with the indication attribute represented by the text string "antihypertensive," and that this attribute is associated with the target drug. It may also be illustratively assumed that the reference drug has an indication attribute "antidepressant" that has a numerical value 15 associated with it. A quantitative comparison may be made dichotomously, i.e., 12 does not equal 15, so the score is 0. In one of many other variations, the numerical values may be assigned so as to reflect some measure of similarity, such as N-gram or edit distance, so that the commonality of the letters "anti" are the reason that the values 12 and 15 are coded to be closer to each other than would be the case if there were no such commonalities. This coding may be done automatically, such as by name attribute comparator 410, based on orthographic, phonetic, and/or phonological analyses of the text string. Alternatively, the reason that indication values of two drugs are relatively close to each other may be that they have somewhat similar uses, such as "antidepressant" and "anti-anxiety." In these kinds of arrangement, i.e., where values are closer together if similar based on selected criteria, the value of the similarity score generated by comparator 610 may be inversely related to the distance between the values, or some other formula may be used.

Dosage form comparator 615. Dosage form comparator 615 generates one or more product-attribute similarity scores 422 based at least in part on one or more dosage forms of the target and reference drugs. Some typical values for this product attribute include "tablet," "capsule," "solution," "suppository," and so on. These values may be coded and/or compared in any of a variety of ways, including those described above with respect to comparator 610.

Administration route comparator 620. Administration route comparator 620 generates one or more product-attribute similarity scores 422 based at least in part on one or more administration routes of the target and reference drugs. Some typical values for this product attribute include "oral," "nasal," "sublingual," and so on. These values may be coded and/or is compared in any of a variety of ways, including those described above with respect to comparator 610.

Manufacturer comparator 625. Manufacturer comparator 625 generates one or more product-attribute similarity scores 422 based at least in part on one or more manufacturers of the target and reference drugs. Some typical values for this product attribute include "Searle," "Lilly," "Merck," and so on. These values may be coded and/or compared in any of a variety of ways, including those described above with respect to comparator 610.

Pharmacological category comparator 630. Pharmacological category comparator 630 generates one or more product-attribute similarity scores 422 based at least in part on one or more pharmacological categories of the target and reference drugs. Some typical values for this product attribute include "benzodiazapines," "selective serotonin reuptake inhibitors," and so on. These values may be coded and/or compared in any of a variety of ways, including those described above with respect to comparator 610.

Storage requirements comparator 635. Storage requirements comparator 635 generates one or more product-attribute similarity scores 422 based at least in part on one or more storage requirements of the target and reference drugs. Some typical values for this product attribute include "refrigerated," "in the dark," "in the emergency room," and so on. These values may be coded and/or compared in any of a variety of ways, including those described above with respect to comparator 610.

Color comparator 640. Color comparator 640 generates one or more product-attribute similarity scores 422 based at least in part on one or more colors of the target and reference drugs. Typical values for this product attribute are evident, and they may be coded and/or compared in any of a variety of ways, including those described above with respect to comparator 610. In addition, particular aspects of cognitive processing related to visual processing may be included in the coding and/or comparison operations. For example, there may be experimental evidence that certain colors are more likely to be confused than others, or that people who have certain types of color blindness are more prone to confusing certain colors.

Shape comparator 645. Shape comparator 645 generates one or more product-attribute similarity scores 422 based at least in part on one or more shapes of the target and reference drugs. Typical values for this product attribute are evident, and they may be coded and/or compared in any of a variety of ways, including those described above with respect to comparator 610.

Legal standing comparator 650. Legal standing comparator 650 generates one or more product-attribute similarity scores 422 based at least in part on one or more legal standings of the target and reference drugs. Some typical values for this product attribute include "prescription only," "over the counter," and so on. These values may be coded and/or compared in any of a variety of ways, including those described above with respect to comparator 610.

Trademark description comparator 655. Trademark description comparator 655 generates one or more product-attribute similarity scores 422 based at least in part on one or more goods and services trademark descriptions of the target and reference drugs. Some typical values for this product attribute include the text typically included in the "goods and services description" field of the trademark database maintained by the U.S. Patent and Trademark Office. These values may be coded and/or compared in any of a variety of ways, including those described above with respect to comparator 610. Also, any of a variety of known or future techniques for morphological, syntactic, and/or linguistic analysis may be used to identify key words from the trademark descriptions that may then be coded or otherwise processed in any of a variety of ways to yield an appropriate value for this trademark description attribute. As one non-limiting example, key words may be identified and the value of the trademark description product attribute for a drug may be a text string formed by a concatenation of these words, their roots, or their morphological components. Any of a variety of orthographic techniques, such as N-gram or edit distance, may be used to generate a quantitative score of the similarity of the text strings for the target and reference drugs.

Schedule comparator 660. Schedule comparator 660 generates one or more product-attribute similarity scores 422 based at least in part on one or more schedules or dosage intervals of the target and reference drugs. Some typical values for this product attribute include "twice per day," "every 6 hours," and so on. Such values may be converted to a common reference period, such as one-day intervals. In such an embodiment, the schedule value for a drug with a prescribed dosage of "twice per day" is two while the schedule value for a drug with a prescribed dosage of "every 6 hours" is four. These values may be coded and/or compared in any of a variety of ways, including those described above.

ATTRIBUTE SIMILARITY SCORES PROCESSOR 430

In the illustrated embodiment, attribute similarity scores processor 430 optionally generates processed attribute similarity scores 312 based on attribute similarity scores 432. Attribute similarity scores 432 include, in the illustrated embodiment, name-attribute similarity scores 412 and product-attribute similarity scores 422. This processing may be accomplished in accordance with any of a variety of known techniques, or techniques to be developed in the future, for combining and/or presenting quantitative information. In some implementations, there need not be an attribute similarity scores processor 430. Rather, as indicated by data flow lines 413 and 423 of FIG. 4, name-attribute similarity scores 412 and product-attribute similarity scores 422 need not be processed. In these alternative implementations, processed attribute similarity scores 312 are generally the same as name-attribute similarity scores 412 and product-attribute similarity scores 422, and a reference to scores 312 may be understood to be the same as a reference to scores 412 and/or scores 422.

It is now illustratively assumed that name-attribute similarity scores 412 and product-attribute similarity scores 422 are provided to attribute similarity scores processor 430 for processing. To provide one example of how this processing may be accomplished, it further is assumed that shape comparator 645 generates a product-attribute similarity score 422 for shape (hereafter referred to for convenience as "shape score 422") having the quantitative value 0.77 to represent a normalized similarity in shapes between target drug A and reference drug B. The illustratively assumed normalization scheme is such that a score of 0.00 indicates the lowest possible similarity (lowest likelihood of confusion) and a score of 1.00 indicates the highest possible similarity (highest likelihood of confusion, e.g., the shapes are identical). Similarly, it is assumed that color comparator 640 generates a product-attribute similarity score 422 for color (hereafter referred to for convenience as "color score 422") having the quantitative value 0.57 to represent a normalized similarity in colors between target drug A and reference drug B. For purposes of clarity, it is assumed that product attribute comparator 420 in this illustrative example includes only shape comparator 645 and color comparator 640. In this example, it is assumed that name attribute comparator 410 has generated a name-attribute similarity score 412 (hereafter referred to for convenience as "name score 412") having a value of 0.30 based on the names of drugs A and B in target-reference data 222.

Attribute similarity scores processor 430 thus operates on name score 412, shape score 422, and color score 422 to produce processed attribute similarity score 312 for target drug A and reference drug B. For example, the value of 0.30 for name score 412, the value of 0.77 for shape score 422, and the value of 0.57 for color score 422 may be averaged to generate a processed attribute similarity score 312 having a value of (0.30+0.77+0.57)/3=0.55.

Any other statistical or other known or future technique for combining, listing, concatenating, correlating, associating, and/or otherwise processing quantitative values also may be used. For example, it may be predetermined, or indicated by user 102 in accordance with known techniques such as a graphical user interface, that the shape of a drug is twice as important as either the color or name of a drug with respect to whether that drug is confused with another drug. In this case, one way in which attribute similarity scores processor 430 may generate a processed attribute similarity score 312 is to weight the value of 0.77 for shape score 422 by multiplying it by 2 (because it is twice as important as the value for color score 422 or name score 412) to yield a weighted shape score 422 of 1.54. Averaging this weighted value with the value of 0.57 for color score 422 and 0.30 for name score 412 yields a processed attribute similarity score 312 of (0.30+1.54+0.57)/3=0.80. Alternatively, the value of shape score 422 may be counted twice, yielding a processed attribute similarity score 312 of (0.30+0.77+0.77+0.57)/4=0.60. As will be evident to those skilled in the relevant art, there are numerous ways for applying weighting and/or other processing schemes, for combining the results of these schemes, and for presenting the results for display to a user or for additional processing. For example, rather than averaging scores, they may simply be concatenated in a list so that, for example, processed attribute similarity scores 312, using weighting, has the value "name score=0.30; shape score=1.54; color score=0.57." Also, as noted, attribute similarity scores processor 430 need not be used in some implementations so that, for example, processed attribute similarity scores 312 has the value "name score=0.30; shape score=0.77; color score=0.57."

SEVERITY OF CONFUSION SCORES GENERATOR 320

As noted, severity of confusion scores generator 320 generates one or more severity of confusion scores 322 representing a severity of confusion between the target and reference drugs. With respect to embodiments involving method steps, the operations of severity of confusion scores generator 320 generally are represented by step 1050 labeled "generate severity of confusion scores."

The term "severity of confusion" refers to the consequences to the patient of confusing a target and reference drug. Some errors may be relatively benign, while others may have serious or fatal consequences. In one implementation of the illustrated embodiment, each record in drug attribute database 214 includes a field that contains a value representing a measure of the potential severity of confusing the drug corresponding to that record with another drug. There are a number of forms that this value, hereafter referred to as the "severity of confusion value," may take, and a number of ways that it may be used by generator 320 to generate a severity of confusion score 322 for a particular target-reference pair. As may be the case with any other field of database 214, the values entered in the records of this database may be (by way of example and not limitation) entered by user 102 using an input device of input-output devices 160, included in local update information 172 and/or remote update information 174, or computed based on other fields of database 214.

In one implementation, the severity of confusion value of a drug may be a scalar value representing the drug's toxicity. Thus, for example, the value may be 0 if the drug is harmless to take under any conditions (e.g., in any dosage strength or form), 9 if it is highly toxic and may cause serious negative effects if not taken precisely as intended, and 10 if it will cause serious negative effects even if taken as intended. For illustration, it may be assumed that target drug A has a severity of confusion value of 2 and reference drug B has a severity of confusion value of 9. Generator 320 may generate a severity of confusion score 322 for this target-reference pair relying primarily or entirely on the severity of confusion value of reference drug B. For example, score 322 may be 9, indicating a high severity of confusing drug B for drug A. One rationale for this approach is that any use of a highly toxic drug when not intended is likely to have severe consequences. Conversely, it may be presumed that the use of a non-toxic drug when not intended is not likely to have severe consequences. However, this latter presumption is likely to be wrong in many cases, since the failure to administer the intended drug may have severe negative consequences (e.g., because the desired treatment was not obtained or a treatment regimen was disrupted) even though the administration of the unintended drug did not, per se, have negative consequences.

Alternatively, score 322 may be derived by using any known measure of distance between the severity of confusion values of the target and reference drugs, such as substracting 2 from 9 to yield a score 322 of 7. However, this latter approach generally fails to take into consideration the obvious fact that substituting one highly toxic drug (e.g., having a severity of confusion value of 9) for another highly toxic drug (e.g., also having a severity of confusion value of 9) may have severe consequences even though the difference between the two scalar values representing degrees of toxicity is small or zero.

Therefore, in alternative implementations, the severity of confusion value may be a vector value; i.e., a value having two or more components, each capable of having a scalar (or another vector) value. For example, the value of one component may represent toxicity if taken in a particular dosage form (e.g., one that involves ingestion), the value of another component may represent toxicity if taken in another dosage form (e.g., by use of a suppository). Additional components may represent toxicity if erroneously used in place of a drug intended to act as an antidepressant, in place of a drug intended to depress the immune system, in place of a drug intended to lower blood pressure, and so on. As one of skill in the relevant arts will now appreciate, a vector value taking into account even a substantial portion of possibly relevant factors, and combinations thereof, is likely to have many components and may require relatively complex computations to generate a severity of confusion score 322. Nonetheless, a variety of known techniques for storing vector information and manipulating vector values may readily be applied. For example, matrices may be used to store the vector information and matrix algebra and/or other techniques may be applied by severity of confusion scores generator 322.

In yet other implementations, the severity of confusion value for each drug may be a vector value having components corresponding to all, or a portion, of the other drugs in drug attribute database 214. For example, it may illustratively be assumed that database 214 contains records for three drugs, A through C. The severity of confusion values for these drugs, in one aspect, may be based on the presumption that the drug corresponding to the record containing the severity of confusion values is the target drug. Each of the values has a component having a value representing the severity of confusing the target drug with each possible reference drug. An illustrative arrangement of this approach is shown in the following Table 1.

TABLE 1

Illustrative Severity of Confusion Values

| Target Drug | Reference Drug | | |
|---|---|---|---|
| | A | B | C |
| A | — | 8 | 3 |
| B | 2 | — | 0 |
| C | 1 | 4 | — |

Thus, with reference to the examples of Table 1, the severity of confusion value associated with erroneously dispensing drug B (the reference drug) instead of drug C (the target drug) is 4. The severity of confusion value associated with erroneously dispensing drug C (the reference drug) instead of drug B (the target drug) is 0. Severity of confusion scores generator 320 may generate a severity of confusion score 322 by using a known technique, such as search and compare, to find the appropriate severity of confusion value in view of the identities of the target and reference drugs as indicated by target-reference data 222. Using the current example provided in Table 1, if generator 325 determines, based on data 222, that the target drug is drug B and the reference drug is drug C, then generator 325 determines by any of a variety of known techniques, such as parsing the vector severity of confusion value of target drug B, that the severity of confusion score 322 is equal to the component of target drug B's severity of confusion value corresponding to reference drug C. That is, in this example, the severity of confusion score 322 is the value 0.

Figure 7:
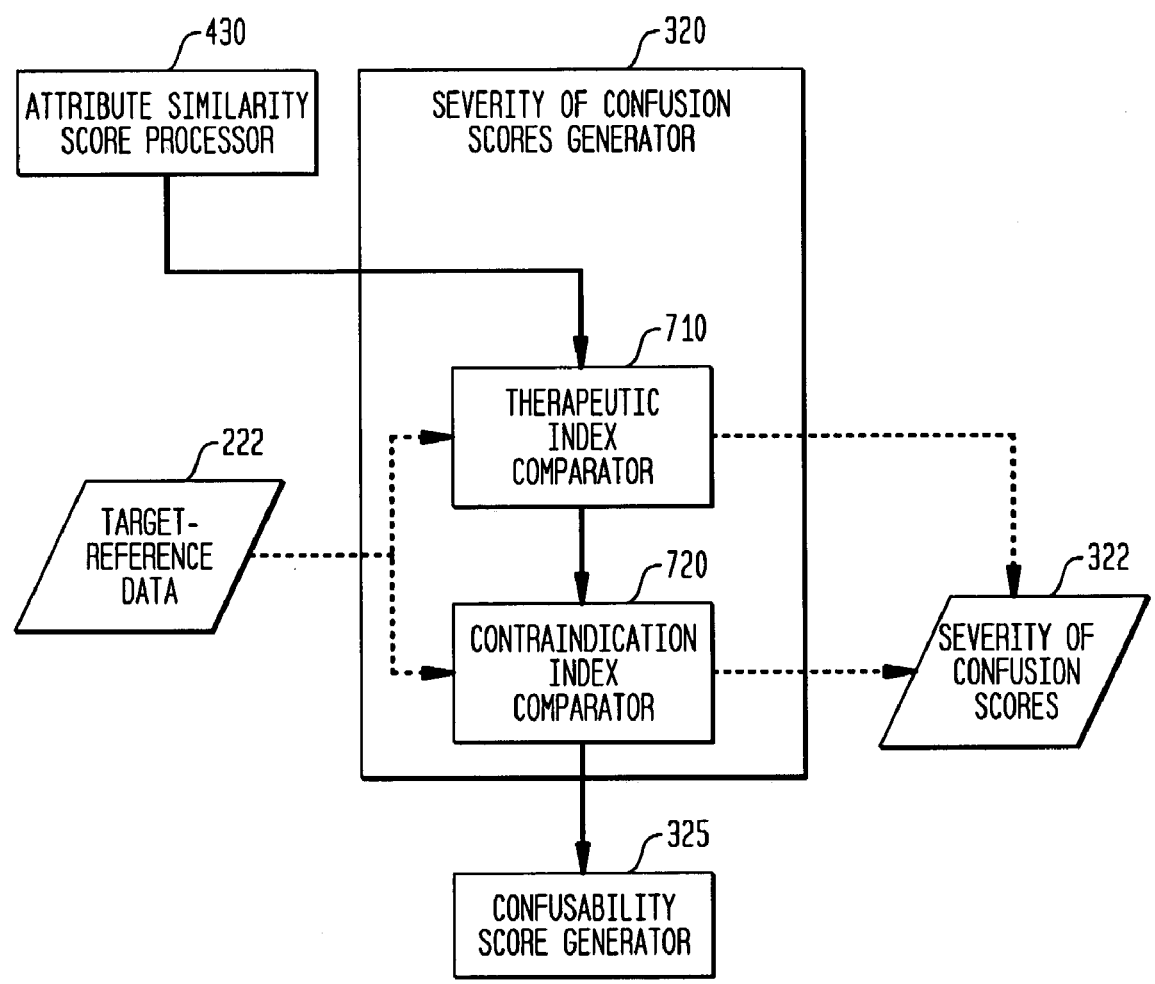
FIG. 7 is a functional block diagram of one embodiment of a severity of confusion scores generator of the composite analyzer of FIG. 3A.

Many other schemes for determining severity of confusion scores 322 are possible. For example, FIG. 7 is an illustrative embodiment in which severity of confusion scores generator 320 includes therapeutic index comparator 710 and contraindication index comparator 720. Comparator 710 operates on attribute information in target-reference data 222 that represents a therapeutic index for the target and a therapeutic index for the reference drug. The therapeutic index of a drug may be obtained from commercial sources, governmental sources, developed by experts, or otherwise derived based on experiment, analysis, or other known techniques. The therapeutic index is a measure of how safe it is to vary the dose of a drug. For example, if a drug must be administered within a narrow range of doses to be safe, then a value may be given to the therapeutic index that indicates that the severity of confusion for this drug, in this respect, is relatively high.

For instance, the drugs Cisplatin and Carboplatin are both used in chemotherapy treatments for cancer. A typical dosage for Cisplatin is 100 milligrams, and a typical dosage for Carboplatin is 450 milligrams. Fatal results are likely to occur if Cisplatin is erroneously administered in a dosage of 450 milligrams, as might occur, for example, if it is confused with Carboplatin. The record for Cisplatin in database 214 and, thus, in target-reference data 222 if it is a target or reference drug, includes an attribute field for its therapeutic index that has a high value. Comparator 710 thus may generate a severity of confusion score 322 that is relatively high if Cisplatin is the target and/or the reference drug. Also, score 322 may be generated based on a mathematical and/or logical comparison of the therapeutic indexes of the target and reference drugs.

Contraindication index comparator 720 operates in a similar manner based on attribute fields of the target and reference drugs that contain values indicative of a contraindication index for those drugs. A contraindication index may be derived from similar sources to those noted above with respect to the therapeutic index. It relates to severity of confusion due to the interactive affects of a drug. That is, some drugs are more prone than others to producing negative consequences due to interactions. Thus, a high value for the contraindication index of a drug may indicate that the drug has a high likelihood of interacting with other drugs to produce negative effects on a patient. Comparator 720 thus may generate a severity of confusion score 322 that is relatively high if the target and/or the reference drug has a high value for its attribute indicative of its contraindication index. Also, score 322 may be generated based on a mathematical and/or logical comparison of the contraindication indexes of the target and reference drugs.

CONFUSABILITY SCORE GENERATOR 325

As noted, confusability score generator 325 generates, for each of one or more target drugs, one or more processed target confusability scores 327 representing the confusability of the target drugs. The word "confusability" in this context refers to a measure of whether the target drug is likely to be confused with other drugs (not just with a single reference drug or a composite of reference drugs). Confusability thus is an attribute of the target drug generated by comparing attributes of the target drug with a large population of other drugs with respect to which comparable attribute information is available. "Confusability" is thus to be distinguished from "likelihood of confusion," which is used herein interchangeably with "similarity," to indicate a measure of comparison between the attributes of a target drug (or composite of target drugs) and a reference drug (or composite of reference drugs).

Figure 8:
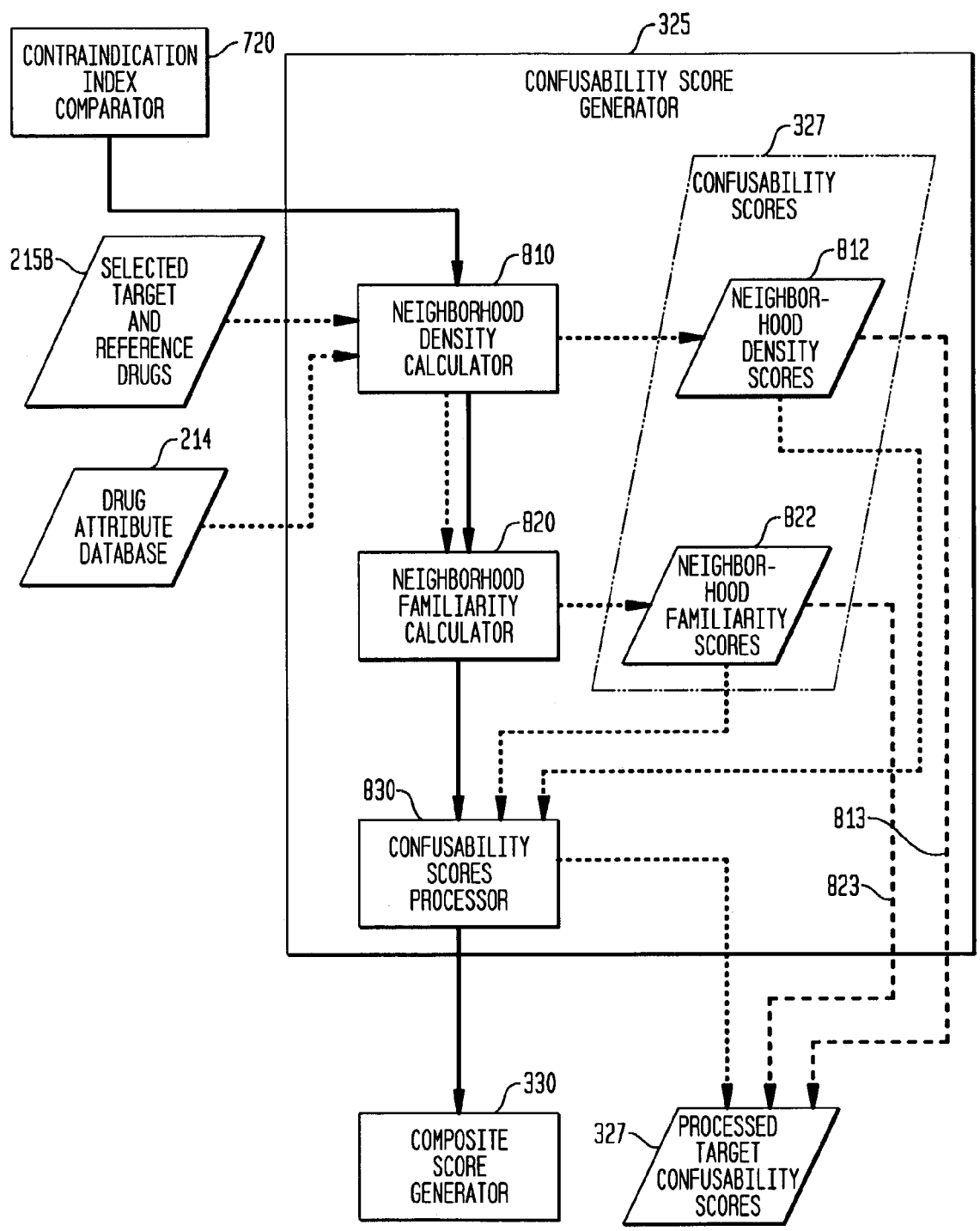
FIG. 8 is a functional block diagram of one embodiment of a confusability score generator of the composite analyzer of FIG. 3A.

FIG. 8 is a functional block diagram of confusability score generator 325. As shown in FIG. 8, generator 325 in the illustrated embodiment includes neighborhood density calculator 810 that calculates one or more neighborhood density scores 812 for the target drug, neighborhood familiarity calculator 820 that calculates one or more neighborhood familiarity scores 822 for the target drug, and confusability scores processor 830 that optionally processes scores 812 and 822 to generate one or more processed target confusability scores 327. (With respect to embodiments involving method steps, these operations of confusability score generator 325 generally are represented by step 1060 labeled "generate target confusability scores.")

NEIGHBORHOOD DENSITY CALCULATOR 810

Neighborhood density calculator 810 generates one or more confusability scores 327 for a target drug. Each score is based at least in part on the number of population drugs within a specified "neighborhood" around the target drug. The word "neighborhood" in the context of calculator 810 (and calculator 820, described below) refers to an area around a target drug (or composite of a number of target drugs). The word "area" is used as a geometric metaphor indicating proximity to the target drug in N-dimensional space. Thus, in a 3-dimensional space, an area constituting a neighborhood would be a 3-dimensional volume within which the target drug is contained.

The number of dimensions may be as many as the total number of attributes (i.e., all name and product attributes) for drugs in drug attribute database 214. Typically, but not necessarily, however, the dimensionality of the attribute space operated upon by neighborhood density calculator 810 corresponds to the number of attributes of the target and population drugs that bear on perception. For example, name, color, and shape are all attributes of this type because they are attributes that are perceived by persons dispensing or otherwise using the drugs. Distance along each of the axes of the attribute space is a function of the values of the attribute corresponding to the axis. The measure of distance may be Euclidean, weighted Euclidean, or non-Euclidean. With respect to the illustrated embodiment, there may be an axis for any one or more of the name attributes associated with analyzers 510 through 530 and product attributes associated with any of comparators 605 through 660. In alternative embodiments, there may be other axes corresponding to other name and/or product attributes.

Figure 9:
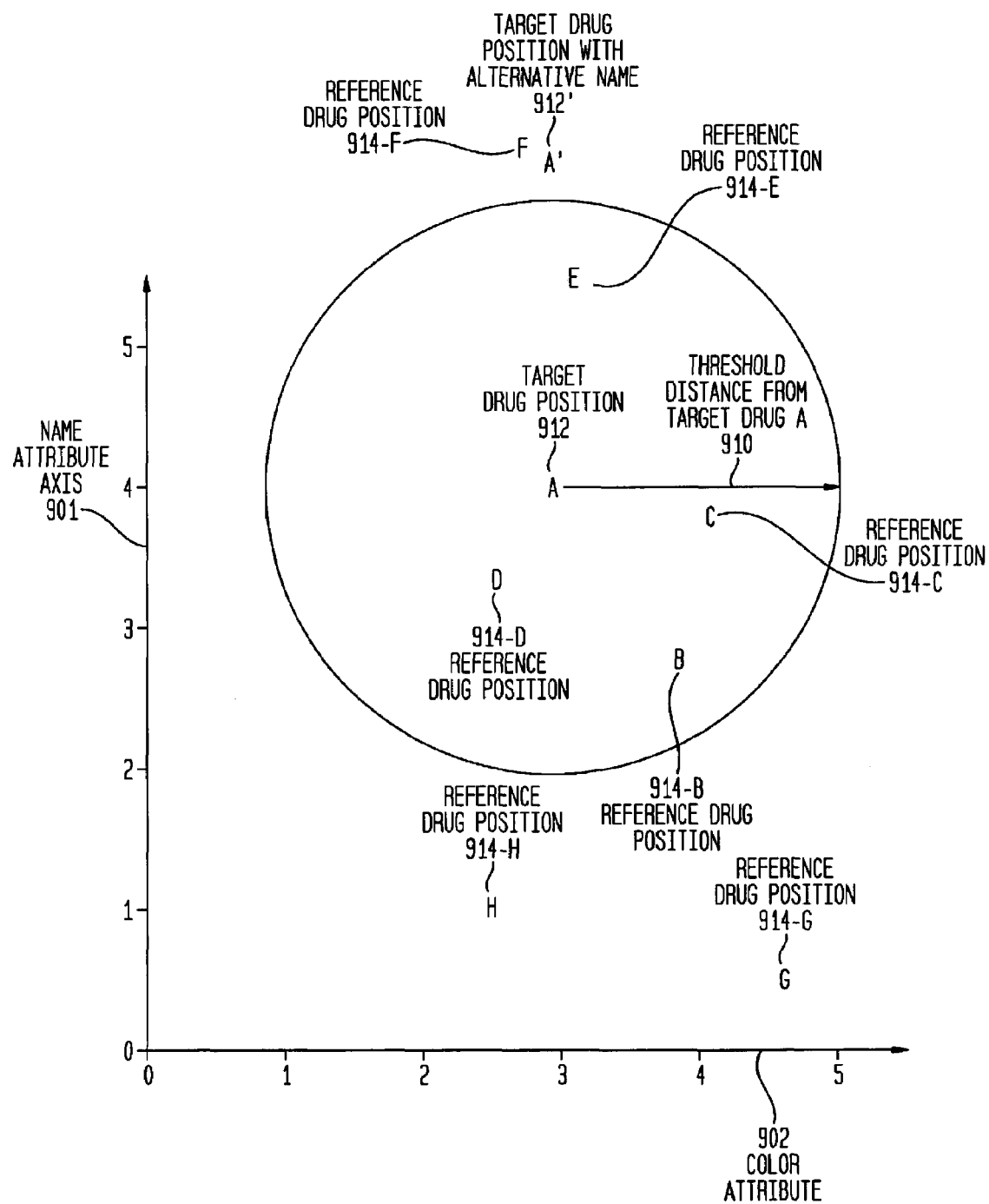
FIG. 9 is a graphical representation of one embodiment of an illustrative 2-dimensional attribute space, showing positions of a target drug and a population of other drugs, for processing by one embodiment of a confusability score generator of the composite analyzer of FIG. 3A.
Figure 10:
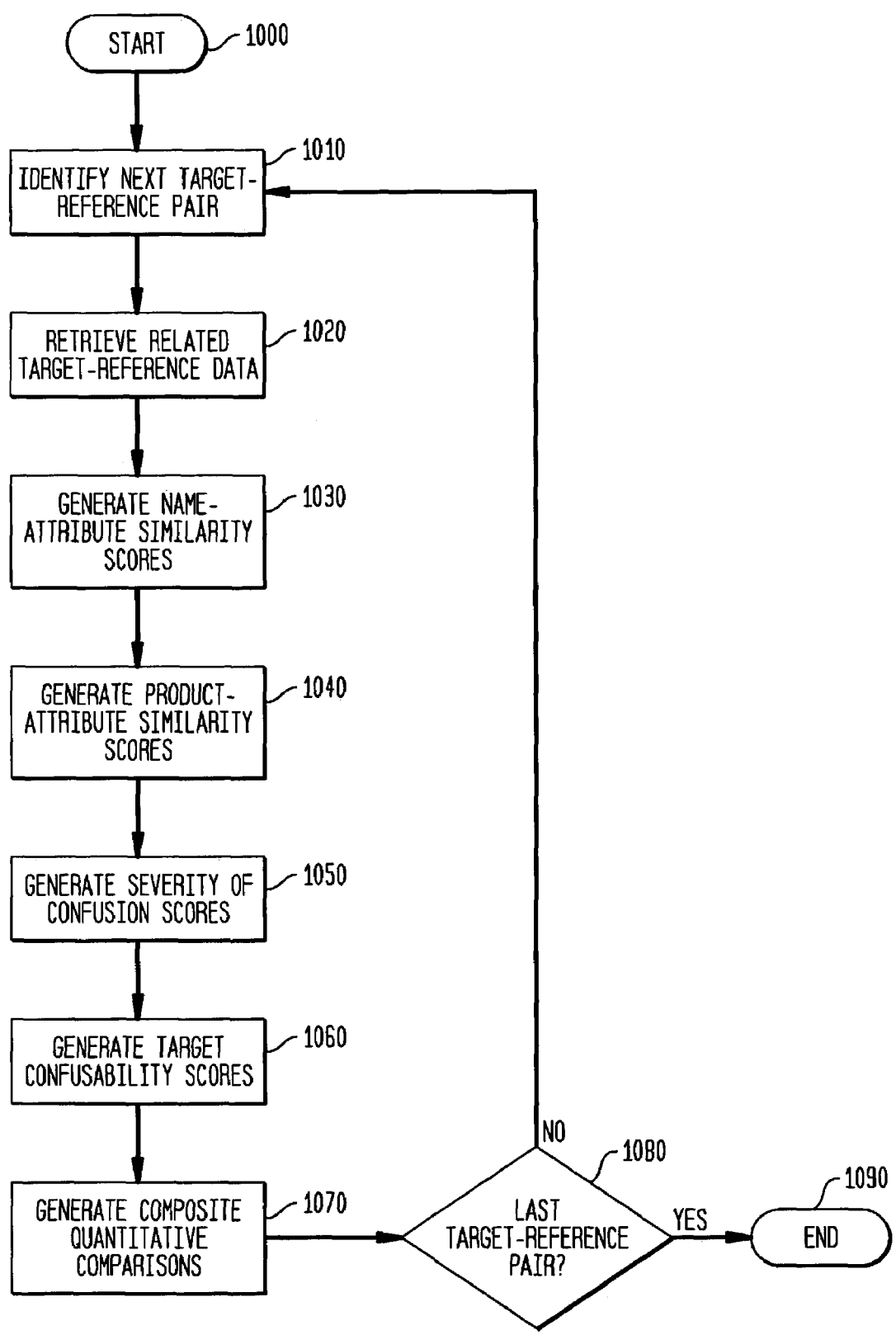
FIG. 10 is a simplified flow diagram of one embodiment of a method for comparing target and reference drugs.

FIG. 9 is a graphical representation of an illustrative 2-dimensional attribute space, showing positions of a target drug A (labeled as target drug position 912) and reference drugs B through H (labeled as reference drug positions 914-B through 914-H, respectively). The 2-dimensional space is defined by horizontal axis 902 representing values of color attributes of the drugs in drug attribute database 214, and a vertical axis 901 representing values of name attributes of the drugs in drug attribute database 214. An area in this 2-dimensional space constituting a "neighborhood" around target drug A is determined in this illustrative example by drawing a circle around target drug position 912 having a radius equal to a "threshold distance" from target drug A. The magnitude of threshold distance 910 of this example may be predetermined based on experimental data regarding the likelihood of confusion of drugs based on their colors and names, on statistical calculations regarding average density distributions of drug positions in this 2-dimensional space, or in other ways. Also, the magnitude of threshold distance 910 may be selected by user 102 using a graphical user interface or any of a variety of other known techniques. Further, it will be understood that the area constituting the neighborhood around target drug A need not be a circle (or an N-dimensional extension of a circle). Rather, it may be any shape, as may be determined by various alternative ways of determining or selecting the threshold distance to vary in magnitude. For example, the threshold distance may have values such as to describe a perimeter of plus or minus 2 from position 912 along the horizontal axis and plus or minus 1 from position 912 along the vertical axis, thus determining a neighborhood area that is a rectangle with target drug position 912 at its center.

Neighborhood density calculator 810 uses any of a variety of known techniques, such as coordinate-comparison techniques, to count the number of reference drugs in the total population of drugs B-H that are positioned inside the neighborhood around the target drug. For example, with respect to FIG. 9, calculator 810 determines that reference drugs B through E are positioned within the neighborhood of target drug A because their positions are within the circle having target drug position 912 at its center and its perimeter determined by a radius having a threshold distance 910. The positions of reference drugs F–H are outside of the neighborhood because they are outside of that circle. The neighborhood density score 812 for target drug A in this exemplary 2-dimensional space thus has the value 4, corresponding to the four reference drugs, B–E, positioned within the neighborhood. Generally speaking, the higher the value of neighborhood density score 812, the greater the likelihood that target drug A will be subject to confusion with other drugs with respect to the combination of their respective names and colors. This greater likelihood of confusion is due to the fact that the combination of target drug A's name and color is less distinct than the combination of the name and color of another drug having a smaller neighborhood density score 812. It will be understood that the population of drugs in FIG. 9 is shown to be relatively small, only seven drugs, B–H, not counting the target drug A, for purposes of clarity. The population in many implementations will include all drugs in drug attribute database 214, not including the target drug.

A neighborhood density score 812 calculated by neighborhood density calculator 810 for a particular target drug may be considered as an attribute of that target drug. One target drug therefore may be compared to another target drug based on their respective density scores 812. In contrast, comparators 410 and 420 typically generate comparisons of user-selected target drugs with user-selected reference drugs. They therefore generate measures of similarity, or likelihood of confusion, between a target and a reference drug rather than computing an attribute of the target drug.

One context in which the neighborhood density score of a target drug thus may be particularly relevant is in considering the desirability of alternative names for a new drug. It will be assumed for illustrative purposes that the color of the drug will be the same irrespective of the name that is chosen. For one name, such as represented by the component of target drug position 912 projected on name attribute axis 901, the neighborhood density score is, as noted, 4. For an alternative name, such as represented by target drug position 912' and indicated by the label A' in FIG. 9, the neighborhood density score 812 may be different. If, as is the case in the illustrative example of FIG. 9, score 812 is less for the alternative name, then this factor may influence the determination of which name to choose for the drug. A target drug's neighborhood density score 812 therefore may be included in composite quantitative comparison 216 to facilitate decisions of this type, or more generally to provide a quantitative and deterministic measure of the confusability of the target drug as compared with the confusability of other target drugs.

It will be understood that each target drug may have many neighborhood density scores 812; for example, different ones for different numbers or combinations of attributes used to determine the dimensionality of the attribute space. Also, different scores 812 may be generated by neighborhood density calculator 810 by using different values of a threshold distance, by different schemes for correlating the number of drugs positioned within the neighborhood to a score 812 (e.g., determining a weighted count based on distance rather than a count in which all positions within the neighborhood are counted equally), or combinations of these alternatives.

NEIGHBORHOOD FAMILIARITY CALCULATOR 820

Neighborhood familiarity calculator 820 calculates one or more neighborhood familiarity scores 822 for the target drug. The operations of calculator 820 in the illustrated embodiment are similar to those of calculator 810 as described above. In particular, a neighborhood is determined around the selected target drug in an N-dimensional attribute space where N is a number of name and/or product attributes, the values of each of which typically are represented by one axis in the attribute space. As in the case of the operations of calculator 810, the neighborhood may be determined by using a constant or variable threshold distance measured from the position of the selected target drug in the attribute space. Thus, the same example used with respect to calculator 810, shown in FIG. 9, may be used with respect to the operations of calculator 820. In this example, the neighborhood around target drug A at target drug position 912 is the interior of the circle circumscribed by a radius centered on position 912 and having a length equal to threshold distance 910. As before, the reference drugs within this neighborhood are reference drugs B–E.

Neighborhood familiarity calculator 820 calculates one or more neighborhood familiarity scores 822 for target drug A based on a measure of the familiarity of each of the reference drugs. A reason for calculating neighborhood familiarity scores 822 is related to certain cognitive effects, aspects of which were described above with respect to the operations of phonological analyzer 530. As noted, infrequently encountered words tend to be confused with similar words that are more frequently encountered, and this effect appears to become more important as the stimulus is degraded. These cognitive effects, however, need not be limited to confusion based on the similar names (i.e., similar sounding or similar looking) of drugs, as discussed above with respect to phonological analyzer 530. Rather, confusion due to familiarity (i.e., confusing a relatively unfamiliar drug with a relatively familiar one) may be based on a variety of perceptual errors involving attributes other than, or in addition to, name attributes. For example, the likelihood of erroneously administering drug B instead of the intended drug A in an emergency room situation may increase if, in addition to having names that are similar, drug B is frequently stored in an emergency room cart whereas drug A is not. This error may increase if the person making the error in administration is distracted due to other events in the emergency room, thus resulting in degraded stimuli with respect to the name and/or storage-requirement attributes of the intended drug A.

In one implementation of neighborhood familiarity calculator 820, each drug, i.e., each record, in drug attribute database 214 includes an attribute that is indicative of the familiarity of that drug. For example, the frequency of prescription of a drug is one proxy for familiarity because the more often a drug is prescribed, the more familiar doctors, nurses, pharmacists, and others are likely to be with the drug. An advantage of using frequency of prescription as a proxy for familiarity is that data generally is available from both governmental and commercial sources regarding the frequency of prescription of many drugs. For example, this data is available from the National Ambulatory Medical Care Survey conducted annually by the U.S. National Center for Health Statistics (see Internet web site at www.cdc.gov/nchswww/), or from commercial sources such as IMS (see Internet web site at www.Imshealth.com/html/marketresearch.htm). Alternative proxies may be used, such as measures of familiarity derived from surveys, experiments, focus groups, and the products of any of a variety of other techniques known to social scientists for measuring cognitive characteristics such as familiarity. Any of these measures of familiarity may be either scalar or vector quantities. That is, a drug may have one measure of familiarity (having a scalar quantity) that is used by calculator 820 irrespective of the combination of attributes that define the attribute space. Alternatively, a drug may have many measures of familiarity (vector quantities) depending on the attributes that define the attribute space. Thus, if the attribute space is defined in part by the name attribute, one measure of familiarity (such as frequency of prescription) may be used; if the attribute space is defined in part by the storage-requirement attribute, another measure of familiarity (familiarity of a user population with the use of drugs under various storage conditions) may be used.

For illustrative purposes, it is now assumed that, for target drug A and each of reference drugs B–H in FIG. 9, there is a frequency-of-prescription attribute in database 214 that serves as a proxy for familiarity. It will be assumed that the higher the value of this attribute, the greater the frequency of prescription and thus, presumably, the greater the familiarity of the drug. In one of many possible implementations, neighborhood familiarity calculator 820 calculates a dichotomous value for target drug A's neighborhood familiarity score 822 by comparing the frequency-of-prescription attribute of drug A with the frequency-of-prescription attributes of the reference drugs in drug A's neighborhood, i.e., drugs B–E. If at least one of drugs B–E have a frequency-of-prescription attribute that is greater than that of target drug A, then target drug A is given a score 822 that indicates a high neighborhood frequency, e.g., the value 1. If all of drugs B–E have a frequency-of-prescription attribute that is less than or equal to that of target drug A, then target drug A is given a score 822 that indicates a low neighborhood frequency, e.g., the value 0. Many variations on this dichotomous approach are possible, such as assigning a high neighborhood frequency value to score 822 if a majority of the reference drugs have a higher frequency-of-prescription attribute than that of the target drug. Many other formulas and approaches are possible, including ones in which the frequency-of-prescription attributes of the reference drugs are weighted by factors such as their distance from target drug A. Also, score 822 may have continuous values. For example, neighborhood frequency calculator 820 may calculate an average of the frequency-of-prescription attributes of the reference drugs in the neighborhood, or an average of these attributes weighted by distance from the target drug, and assign the average value to the target drug's neighborhood familiarity score 822.

As noted above with respect to calculator 810, many scores may be generated for each target drug depending on, among other factors, the attributes that are chosen to define the attribute space. The choice of attribute space, i.e., the choice of which attributes to include as axes in the N-dimensional space, may be predetermined, user-selected, selected to show confusability scores 327 in a predetermined or user-selected range (e.g., the worst-case or best-case scores), in other ways, or any combination thereof.

CONFUSABILITY SCORES PROCESSOR 830

Confusability scores processor 830 optionally processes scores 812 and 822 to generate one or more processed target confusability scores 327. If processor 830 is not invoked, then, as indicated respectively by data path lines 813 and 823, scores 812 and 822 may constitute processed target confusability scores 327. Alternatively, any of a variety of known mathematical and/or logical techniques may be used to process and/or combine scores 812 and 822 to generate scores 327. For example, scores 327 may be a weighted sum of scores 812 and 822, an average of scores 812 and 822, the greater of scores 812 and 822, and so on.

COMPOSITE SCORE GENERATOR 330

As noted, composite score generator 330 generates one or more composite quantitative comparisons 216. (With respect to embodiments involving method steps, this operation of composite score generator 330 generally is represented by step 1070 labeled "generate composite quantitative comparisons.") Comparisons 216 may take numerous forms. For example, a single composite quantitative comparison 216 may be generated for each target-reference pair. As another non-limiting example, numerous composite quantitative comparisons 216 may be generated for each target-reference pair. Also, the content of each of comparisons 216 may be varied. The following examples of composite quantitative comparisons 216 therefore should be understood to be illustrative only, and non-limiting.

FIGS. 3B and 3C are simplified schematic representations of two embodiments of composite quantitative comparisons 216. It will be assumed for illustrative purposes that both comparisons 216 of both figures (i.e., comparisons 216A and 216B, respectively), are generated by composite score generator 330 in relation to a target drug A and a reference drug B, except as otherwise indicated below. Generally, either of comparisons 216A or 216B may be conceptually divided into two sections, labeled sections 302-A and 304-A with respect to comparison 216A and sections 302-B and 304-B with respect to comparison 216B. It will be understood that this division is made for convenience of illustration only. The quantitative information in sections 302-A and 302-B relate to comparisons between target drug A and reference drug B. For convenience, these sections are hereafter collectively referred to as the "target-reference comparison" sections 302. The quantitative information in sections 304-A and 304-B relate to the confusability of target drug A in relation to a generally large population of reference drugs, such as all other drugs in database 214. For convenience, these sections are hereafter collectively referred to as the "target confusability" sections 304.

In illustrative composite quantitative comparisons 216A and 216B, the target confusability sections 304 are the same. In particular, they both include the processed target confusability score 327 for target drug A, as described above with respect to the operations of confusability score generator 325. They both also optionally include attribute information regarding target drug A and all reference drugs (drugs B–H in the illustrated embodiment of FIG. 9) that constituted the population of drugs used in generating score 327. As in FIG. 9, this information may be presented in graphical form, or it may be presented in another form such as numerical tables, a textual report, and so on. The choice of attribute space, i.e., the choice of which attributes to include as axes in the N-dimensional space, may be predetermined, user-selected, selected to show graphical representations of the attributes of drugs A and B in a predetermined or user-selected range (e.g., spaces in which the distances between the position of drug A and the position of reference drugs B–E in the neighborhood of drug A are greatest, or smallest), in other ways, or any combination thereof. More generally, it will be understood that the information in sections 304 (and/or in sections 302) may be presented in any graphical, numerical, and/or textual or other format; may be communicated via any known communication modality (printed, electronic, oral, and so on); and that any or all aspects of the information may be omitted in alternative embodiments of comparisons 216A and/or 216B.

With respect to target-reference comparison sections 302, both comparisons 216A and 216B also include a quantitative comparison referred to as "selected target and reference drugs 215A." As noted above with respect to data flow line 223 of FIG. 2A, this optional component of composite quantitative comparison 216 may be a graphical or other type of representation of the positions of the target-reference pair of drugs A and B in any one or more of the numerous N-dimensional attribute spaces that may be defined for various combinations of attribute axes. For example, a graphical representation such as that shown in FIG. 2D may be included by generator 330 in composite quantitative comparisons 216A and 216B. Similar to the description above of element 215B, the choice of attribute space with respect to element 215A, i.e., the choice of which attributes to include as axes in the N-dimensional space, may be predetermined, user-selected, selected to show graphical representations of the attributes of drugs A and B in a predetermined or user-selected range (e.g., spaces in which the distances between the positions of drugs A and B are greatest, or smallest), in other ways, or any combination thereof.

In comparison 216B, the additional elements of section 302-B are processed attribute similarity scores 312, severity scores 332, and quantitative interpretation 338A. Scores 312 and 332 are described above with respect to the operations of attribute similarity scores generator 310 and severity of confusion scores generator 320, respectively. Quantitative interpretation 338A optionally provides a comparison of score 312 and/or score 332 for a particular target-reference pair to corresponding scores for one or more other target-reference pairs, including all other target-reference pairs. Thus, for example, quantitative interpretation 338A may indicate that the similarity score 312 for the target-reference pair consisting of target drug A and reference drug B is in the $99^{th}$ percentile in comparison to the similarity scores 312 for all other target-reference pairs that may be constructed from database 214. That is, the similarity of target drug A and reference drug B, as measured by score 312, is greater than 99 percent of all other target-reference pairs. Alternatively, score 312 (and/or score 322) for target drug A and reference drug B may be compared to a subset of all other pairs of drugs in database 214, e.g., they may be compared to drugs having a particular value for their "legal standing" attribute. As noted, composite score generator 330 may format scores 312 and 322, and interpretation 338A, in any of numerous ways, such as by presenting them numerically in separate or common tables, in graphical form, in textual form, or in any combination thereof.

As shown in FIG. 3B, comparison 216A includes in section 302-A, in addition to element 215A that has already been described, severity-weighted similarity scores 332 and quantitative interpretation 338B. Composite score generator 330 optionally generates a severity-weighted similarity score 332 for a target-reference pair by weighting and combining one or more of the target-reference pair's attribute similarity scores 432 by the target-reference pair's severity of confusion score 322. This weighting and combining may be accomplished in accordance with any of a variety of known mathematical, logical, or other techniques, by applying adaptive algorithms, or by any other known technique. A reason for combining scores 432 and 322 is that a combined measure of the likelihood of making a mistake, and the severity of making the mistake, may be more useful in identifying dangerous target-reference pairs than either measure alone or both measures considered separately.

Having now described some embodiments of the present invention, it should be apparent to those skilled in the relevant art that the foregoing is illustrative only and not limiting, having been presented by way of example only. For example, many other schemes for distributing functions among the various functional elements of the illustrated embodiment are possible in accordance with the present invention. The functions of any element may be carried out in various ways in alternative embodiments. Also, the functions of several elements may, in alternative embodiments, be carried out by fewer, or a single, element. Similarly, the sequencing of functions or portions of functions generally may be altered. For example, for purposes of clarity the functions of generators 310, 320, and 330 are described as collectively constituting the functions of composite analyzer 230. However, in alternative embodiments, these same functions could be described without reference to a composite analyzer 230. Rather, as one example, generators 310, 320, and 330 could be described directly as components of comparator 100 in the manner in which reference database updater 210 is described as a component of comparator 100. As a further example of alternative configurations of functional elements, the functions of comparators 410 and 420, as described with respect to the illustrated embodiment, could be described as being carried out by a single attribute comparator. Also, in some embodiments, any functional element may perform fewer, or different, operations than those described with respect to the illustrated embodiment. For example, in some embodiments, name attribute comparator 410 may not undertake phonological analysis, or product attribute comparator 420 need not undertake trademark description comparison.

Furthermore, the control flow shown in all of the drawings should be understood generally to be exemplary and not limiting. For example, FIG. 5 shows that analyzer 510 operates and then passes control to analyzer 520, which operates and then passes control to analyzer 520. In alternative embodiments, these analyzers may operate in any other order, they may all operate in parallel, or any other combination of serial and parallel processing may be implemented. Similarly, comparator 420 may pass control to comparator 410, rather than the reverse order shown in FIG. 4, or they may both operate in parallel. The same can be said for the control flow shown among comparators 605–665 in FIG. 6; that is, the order of control may be different, and/or one or more of those comparators may be operated in parallel.

Certain functional elements, data structures, instructions, data, and so on, such as drug attribute database 214, composite quantitative comparison 216, or attribute similarity scores 432, may be described in the above embodiment as being located in memory 130 of user computer 110. In other embodiments, however, they may be located on, or distributed across, computer systems or other platforms that are remote from user computer 110. In those embodiments, the operations of comparator 100 may be carried out over a network or by any of numerous other known means for transferring data and/or control to or from a remote location.

There are many possible variations of the architecture for the data structures referred to above. Data in these data structures may, in alternative embodiments, be saved in different combinations of data structures, or in a single data structure. As will be evident to those skilled in the relevant art, the values in data structures generally are initialized or re-initialized in accordance with any of a variety of known techniques to provide that such values are accurate.

In addition, it will be understood by those skilled in the relevant art that control and data flows between and among functional elements of the invention and various data structures may vary in many ways from the control and data flows described above. More particularly, intermediary functional elements (not shown) may direct control or data flows; the functions of various elements may be combined, divided, or otherwise rearranged, and data may be partitioned, to allow parallel processing or for other reasons; intermediate data structures may be used; various described data structures may be combined; the sequencing of functions or portions of functions generally may be altered; and so on. Numerous other embodiments, and modifications thereof, are contemplated as falling within the scope of the present invention as defined by appended claims and equivalents thereto.

What is claimed is:

1. A drug comparator for assessing the confusability of one or more target drugs and one or more reference drugs based on one or more attributes of each target drug and each reference drug, comprising:
   a name attribute comparator that performs a composite quantitative comparison of a name attribute of the one or more target drugs and the one or more reference drugs, and that generates one or more name-attribute similarity scores based on said comparison, each name-attribute similarity score representing a similarity of the compared name attributes, wherein the name attribute comparator comprises two or more analyzers selected from the group consisting of:
      an orthographic analyzer that generates one or more name-attribute similarity scores based on one or more orthographic measures of the name attributes of the one or more target and reference drugs;
      a phonetic analyzer that generates one or more name-attribute similarity scores based on one or more phonetic measures of the name attributes of the one or more target and reference drugs; and
      a phonological analyzer that generates one or more name-attribute similarity scores based on one or more phonological measures of the name attributes of the one or more target and reference drugs.

2. The drug comparator of claim 1, wherein the name attributes are objective attributes and wherein the composite quantitative comparison performed by the name attribute comparator is deterministic.

3. The drug comparator of claim 1, further comprising:
   a product attribute comparator that performs a composite quantitative comparison of at least one product attribute of the one or more target drugs and the one or more reference drugs, and that generates one or more product-attribute similarity scores based on said comparison, each product-attribute similarity score representing a similarity of the compared product attributes.

4. The drug comparator of claim 3, wherein the product attributes are objective attributes and wherein the composite quantitative comparison performed by the product attribute comparator is deterministic.

5. The drug comparator of claim 1, wherein the one or more orthographic measures comprises one or more measures selected from the group consisting of N-gram measures and edit distance measures.

6. The drug comparator of claim 1, wherein the one or more phonetic measures are determined by phonetically transforming the name attribute of at least one of the target and reference drugs.

7. The drug comparator of claim 6, wherein the one or more phonetic measures are determined by applying an orthographic measure to the phonetically transformed name attribute.

8. The drug comparator of claim 3, wherein the product attribute comparator comprises any one or more comparators selected from the group consisting of:
   a strength comparator that generates at least a first product-attribute similarity score based on one or more dosage strengths of the target and reference drugs;
   an indication comparator that generates at least a second product-attribute similarity score based on one or more indicated uses of the target and reference drugs;
   a dosage form comparator that generates at least a third product-attribute similarity score based on one or more dosage forms of the target and reference drugs;
   an administration route comparator that generates at least a fourth product-attribute similarity score based on one or more administration routes of the target and reference drugs;
   a manufacturer comparator that generates at least a fifth product-attribute similarity score based on one or more manufacturers of the target and reference drugs;
   a pharmacological category comparator that generates at least a sixth product-attribute similarity score based on one or more pharmacological categories of the target and reference drugs;
   a storage requirements comparator that generates at least a seventh product-attribute similarity score based on one or more storage requirements of the target and reference drugs;
   a color comparator that generates at least an eighth product-attribute similarity score based on one or more colors of the target and reference drugs;
   a shape comparator that generates at least a ninth product-attribute similarity score based on one or more shapes of the target and reference drugs;

a legal standing comparator that generates at least a tenth product-attribute similarity score basted on one or more legal standings of the target and reference drugs;

a trademark description comparator that generates at least an eleventh product-attribute similarity score based on one or more goods and services trademark descriptions of the target and reference drugs; and a schedule comparator that generates at least a twelfth product-attribute similarity score based on one or more dosage intervals of the target and reference drugs.

9. The drug comparator of claim 1, further comprising:

a neighborhood density calculator that calculates a neighborhood density score for at least a first target drug of the one or more target drugs based on a number of a first set of reference drugs, wherein each of the first set of reference drugs has a determined distance is from the first target drug that is not greater than a threshold distance, wherein each determined distance is a function of the one or more name-attribute similarity scores.

10. The drug comparator of claim 3, further comprising:

a neighborhood familiarity calculator that calculates a neighborhood familiarity score for at least a first target drug of the one or more target drugs based on a familiarity of the first target drug and the familiarity of each of a first set of reference drugs, wherein each of the first set of reference drugs has a determined distance from the first target drug that is not greater than a threshold distance, wherein each determined distance is a function of the one or more name- or product-attribute similarity scores.

11. The drug comparator of claim 10, wherein the measure of familiarity is determined by using frequency of prescription as a proxy for familiarity.

12. The drug comparator of claim 3,further comprising:

an attribute similarity scores processor that mathematically combines a plurality of attribute similarity scores comprising the group of attribute similarity scores consisting of the one or more name-attribute similarity scores and the one or more product-attribute similarity scores to generate one or more processed attribute similarity scores.

13. The drug comparator of claim 12, wherein at least one of the plurality of attribute similarity scores is associated with a weight, and wherein the attribute similarity scores processor applies the weights to their associated attribute similarity scores prior to combining the attribute similarity scores.

14. The drug comparator of claim 1, further comprising:

a severity of confusion scores generator that generates one or more scores for at least one of the one or more target drugs, each severity of confusion score representing the severity of the consequence to the patient of confusing a target drug for a reference drug.

15. The drug comparator of claim 14, wherein the drug comparator further comprises:

a composite score generator that deterministically generates one or more severity-weighted similarity scores determined by weighting one or more of the attribute similarity scores by one or more of the severity of confusion scores.

16. The drug comparator of claim 14, wherein the severity of confusion scores generator comprises:

a therapeutic index comparator that generates at least a first of the one or more severity of confusion scores based on a therapeutic index of one or more of the target drugs and a therapeutic index of one or more of the reference drugs.

17. The drug comparator of claim 1, wherein when a user selects the one or more target drugs, the drug comparator automatically generates the attribute similarity scores.

18. A drug comparator for assessing the confusability of one or more target drugs and one or more reference drugs based on one or more attributes of each target drug and each reference drug, comprising:

a product attribute comparator that performs a composite quantitative comparison of at least one product attribute of the one or more target drugs and the one or more reference drugs, and that generates one or more product-attribute similarity scores based on said comparison, each product-attribute similarity score representing a similarity of the compared product attributes, wherein the product attribute comparator comprises any one or more comparators selected from the group consisting of:

a strength comparator that generates at least a first product-attribute similarity score based on one or more dosage strengths of the target and reference drugs;

an indication comparator that generates at least a second product-attribute similarity score based on one or more indicated uses of the target and reference drugs;

a dosage form comparator that generates at least a third product-attribute similarity score based on one or more dosage forms of the target and reference drugs;

an administration route comparator that generates at least a fourth product-attribute similarity score based on one or more administration routes of the target and reference drugs;

a manufacturer comparator that generates at least a fifth product-attribute similarity score based on one or more manufacturers of the target and reference drugs;

a pharmacological category comparator that generates at least a sixth product-attribute similarity score based on one or more pharmacological categories of the target and reference drugs;

a storage requirements comparator that generates at least a seventh product-attribute similarity score based on one or more storage requirements of the target and reference drugs;

a color comparator that generates at least an eighth product-attribute similarity score based on one or more colors of the target and reference drugs;

a shape comparator that generates at least a ninth product-attribute similarity score based on one or more shapes of the target and reference drugs;

a legal standing comparator that generates at least a tenth product-attribute similarity score based on one or more legal standings of the target and reference drugs;

a trademark description comparator that generates at least an eleventh product-attribute similarity score based on one or more goods and services trademark descriptions of the target and reference drugs; and a schedule comparator that generates at least a twelfth product-attribute similarity score based on one or more dosage intervals of the target and reference drugs.

19. The drug comparator of claim 18, wherein the product attributes are objective attributes and wherein the composite quantitative comparison performed by the product attribute comparator is deterministic.

20. The drug comparator of claim 18, further comprising:
a name attribute comparator that performs a composite quantitative comparison of a name attribute of the one or more target drugs and the one or more reference drugs, and that generates one or more name-attribute similarity scores based on said comparison, each name-attribute similarity score representing a similarity of the compared name attributes.

21. The drug comparator of claim 20, wherein the name attributes are objective attributes and wherein the composite quantitative comparison performed by the name attribute comparator is deterministic.

22. The drug comparator of claim 20, wherein the name attribute comparator comprises one or more of the group consisting of:
an orthographic analyzer that generates one or more name-attribute similarity scores based on one or more orthographic measures of the name attributes of the one or more target and reference drugs;
a phonetic analyzer that generates one or more name-attribute similarity scores based on one or more phonetic measures of the name attributes of the one or more target and reference drugs; and
a phonological analyzer that generates one or more name-attribute similarity scores based on one or more phonological measures of the name attributes of the one or more target and reference drugs.

23. The drug comparator of claim 18, further comprising:
a neighborhood density calculator for defining a neighborhood around at least a first target drug, the neighborhood defining a proximity to the target drug in N-dimensional attribute space each axis of which corresponds to one attribute, wherein a distance along each axis of the attribute space is a function of the relative values of the attribute corresponding to that axis, the neighborhood density calculator calculating a neighborhood density score for the first target drug based on a number of a first set of reference drugs, wherein each of the first set of reference drugs has a determined distance from the first target drug that is not greater than a threshold distance, wherein each determined distance in the attribute space is a function of the one or more attribute similarity scores.

24. The drug comparator of claim 20, further comprising:
a neighborhood familiarity calculator that calculates a neighborhood familiarity score for at least a first target drug of the one or more target drugs based on a familiarity of the first target drug and the familiarity of each of a first set of reference drugs, wherein each of the first set of reference drugs has a determined distance from the first target drug that is not greater than a threshold distance, wherein each determined distance is a function of the one or more name- or product-attribute similarity scores.

25. The drug comparator of claim 20, further comprising:
an attribute similarity scores processor that mathematically combines a plurality of attribute similarity scores comprising one or more name-attribute similarity scores and one or more product-attribute similarity scores.

26. The drug comparator of claim 20, further comprising:
a severity of confusion scores generator that generates one or more scores for at least one of the one or more target drugs, each severity of confusion score representing the severity of the consequence to the patient of confusing a target drug for a reference drug.

27. The drug comparator of claim 26,
wherein the severity of confusion scores generator comprises a therapeutic index comparator that generates at least a first of the one or more severity of confusion scores based on a contraindication index of one or more of the target drugs and a contraindication index of one or more of the reference drugs.

28. A drug comparator for assessing the confusability of one or more target drugs and one or more reference drugs based on one or more attributes of each target drug and each reference drug, comprising:
a name attribute comparator that performs a composite quantitative comparison of a name attribute of the one or more target drugs and the one or more reference drugs, and that generates one or more name-attribute similarity scores based on said comparison, each name-attribute similarity score representing a similarity of the compared name attributes; and
a product attribute comparator that performs a composite quantitative comparison of at least one product attribute of the one or more target drugs and the one or more reference drugs, and that generates one or more product-attribute similarity scores based on said comparison, each product-attribute similarity score representing a similarity of the compared product attributes, wherein the drug comparator automatically generates the attribute similarity scores upon receipt of an indication of the one or more target drugs.

29. The drug comparator of claim 1, wherein the one or more attributes of the target drug and each reference drug are objective attributes, and wherein the composite quantitative comparisons performed by the name attribute comparator and the product attribute comparator are deterministic.

30. The drug comparator of claim 28, wherein the name attribute comparator comprises one or more of the group consisting of:
an orthographic analyzer that generates one or more name-attribute similarity scores based on one or more orthographic measures of the name attributes of the one or more target and reference drugs;
a phonetic analyzer that generates one or more name-attribute similarity scores based on one or more phonetic measures of the name attributes of the one or more target and reference drugs; and
a phonological analyzer that generates one or more name-attribute similarity scores based on one or more phonological measures of the name attributes of the one or more target and reference drugs.

31. The drug comparator of claim 28, wherein the product attribute comparator comprises any one or more comparators selected from the group consisting of:
a strength comparator that generates at least a first product-attribute similarity score based on one or more dosage strengths of the target and reference drugs;
an indication comparator that generates at least a second product-attribute similarity score based on one or more indicated uses of the target and reference drugs;
a dosage form comparator that generates at least a third product-attribute similarity score based on one or more dosage forms of the target and reference drugs;
an administration route comparator that generates at least a fourth product-attribute similarity score based on one or more administration routes of the target and reference drugs;
a manufacturer comparator that generates at least a fifth product-attribute similarity score based on one or more manufacturers of the target and reference drugs;

a pharmacological category comparator that generates at least a sixth product-attribute similarity score based on one or more pharmacological categories of the target and reference drugs;

a storage requirements comparator that generates at least a seventh product-attribute similarity score based on one or more storage requirements of the target and reference drugs;

a color comparator that generates at least an eighth product-attribute similarity score based on one or more colors of the target and reference drugs;

a shape comparator that generates at least a ninth product-attribute similarity score based on one or more shapes of the target and reference drugs;

a legal standing comparator that generates at least a tenth product-attribute similarity score based on one or more legal standings of the target and reference drugs;

a trademark description comparator that generates at least an eleventh product-attribute similarity score based on one or more goods and services trademark descriptions of the target and reference drugs; and a schedule comparator that generates at least a twelfth product-attribute similarity score based on one or more dosage intervals of the target and reference drugs.

32. The drug comparator of claim 28, further comprising:
a neighborhood density calculator that calculates a neighborhood density score for at least a first target drug of the one or more target drugs based on a number of a first set of reference drugs, wherein each of the first set of reference drugs has a determined distance from the first target drug that is not greater than a threshold distance, wherein each determined distance is a function of the one or more attribute similarity scores.

33. The drug comparator of claim 28, further comprising:
a neighborhood familiarity calculator that calculates a neighborhood familiarity score for at least a first target drug of the one or more target drugs based on a familiarity of the first target drug and the familiarity of each of a first set of reference drugs, wherein each of the first set of reference drugs has a determined distance from the first target drug that is not greater than a threshold distance, wherein each determined distance is a function of the one or more attribute similarity scores.

34. The drug comparator of claim 33, wherein the measure of familiarity is determined by using frequency of prescription as a proxy for familiarity.

35. The drug comparator of claim 28, further comprising:
an attribute similarity scores processor that mathematically combines a plurality of attribute similarity scores to generate one or more processed attribute similarity scores.

36. The drug comparator of claim 35,
wherein at least one of the plurality of attribute similarity scores is associated with a weight, and wherein the attribute similarity scores processor applies the weights to their associated attribute similarity scores prior to combining the attribute similarity scores.

37. The drug comparator of claim 28, further comprising:
a severity of confusion scores generator that generates one or more scores for at least one of the one or more target drugs, each severity of confusion score representing the severity of the consequence to the patient of confusing the at least one target drug for a reference drug.

38. The drug comparator of claim 37, further comprising:
a composite score generator that deterministically generates one or more severity-weighted similarity scores determined by weighting one or more of the attribute similarity scores by one or more of the severity of confusion scores.

39. The drug comparator of claim 37, wherein the severity of confusion scores generator comprises:
a therapeutic index comparator that generates at least a first of the one or more severity of confusion scores based on a therapeutic index of one or more of the target drugs and a therapeutic index of one or more of the reference drugs.

40. The drug comparator of claim 28, further comprising:
a composite score generator that deterministically generates one or more composite quantitative comparisons based on comparisons of one or more attribute-similarity scores.

41. A drug comparator for assessing the confusability of one or more target drugs and one or more reference drugs based on one or more attributes of each target drug and each reference drug, comprising:
a name attribute comparator that performs a composite quantitative comparison of a name attribute of the one or more target drugs and the one or more reference drugs, and that generates one or more name-attribute similarity scores based on said comparison, each name-attribute similarity score representing a similarity of the compared name attributes; and a neighborhood density calculator that calculates a neighborhood density score for at least a first target drug of the one or more target drugs based on a number of a first set of reference drugs, wherein each of the first set of reference drugs has a determined distance from the first target drug that is not greater than a threshold distance, wherein each determined distance is a function of the one or more attribute similarity scores.

42. The drug comparator of claim 41, further comprising:
a product attribute comparator that performs a composite quantitative comparison of at least one product attribute of the one or more target drugs and the one or more reference drugs, and that generates one or more product-attribute similarity scores based on said comparison, each product-attribute similarity score representing a similarity of the compared product attributes.

43. The drug comparator of claim 42, wherein the one or more attributes of the target drug and each reference drug are objective attributes, and wherein the composite quantitative comparisons performed by the name attribute comparator and the product attribute comparator are deterministic.

44. A drug comparator for assessing the confusability of one or more target drugs and one or more reference drugs based on one or more attributes of each target drug and each reference drug, comprising:
a name attribute comparator that performs a composite quantitative comparison of a name attribute of the one or more target drugs and the one or more reference drugs, and that generates one or more name-attribute similarity scores based on said comparison, each name-attribute similarity score representing a similarity of the compared name attributes; and a neighborhood familiarity calculator that calculates a neighborhood familiarity score for at least a first target drug of the one or more target drugs based on a familiarity of the first target drug and the familiarity of each of a first set of reference drugs, wherein each of the first set of reference drugs has a determined distance from the first target drug that is not greater than a threshold distance, wherein each determined distance is a function of the one or more attribute similarity scores.

45. The drug comparator of claim 44, further comprising:
a product attribute comparator that performs a composite quantitative comparison of at least one product attribute of the one or more target drugs and the one or more reference is drugs, and that generates one or more product-attribute similarity scores each product-attribute similarity score representing a similarity of the compared product attributes.

46. The drug comparator of claim 45, wherein the one or more attributes of the target drug and each reference drug are objective attributes, and wherein the composite quantitative comparisons performed by the name attribute comparator and the product attribute comparator are deterministic.

47. The drug comparator of claim 46, further comprising:
a neighborhood density calculator that calculates a neighborhood density score for at least a first target drug of the one or more target drugs based on a number of a first set of reference drugs, wherein each of the first set of reference drugs has a determined distance from the first target drug that is not greater than a threshold distance, wherein each determined distance is a function of the one or more attribute similarity scores.

* * * * *